United States Patent
Gorochov et al.

(10) Patent No.: US 11,718,661 B2
(45) Date of Patent: Aug. 8, 2023

(54) COMPOSITION FOR THE TREATMENT OF ANTIBODY DEFICIENCIES

(71) Applicants: INSERM (Institut National de la Santé et de la Recherche Médicale), Paris (FR); Sorbonne Université, Paris (FR); Assistance Publique-Hôpitaux de Paris (APHP), Paris (FR)

(72) Inventors: Guy Gorochov, Paris (FR); Martin Larsen, Paris (FR); Delphine Sterlin, Paris (FR); Jehane Fadlallah, Paris (FR)

(73) Assignees: INSERM (Instut National de la Santé et de la Recherche Médicale), Paris (FR); Sorbonne Université, Paris (FR); Assistance Publique-Hôpitaux de Paris (APHP), Paris (FR)

( * ) Notice: Subject to any disclaimer, the term of this patent is extended or adjusted under 35 U.S.C. 154(b) by 0 days.

(21) Appl. No.: 17/288,013

(22) PCT Filed: Oct. 29, 2019

(86) PCT No.: PCT/EP2019/079477
§ 371 (c)(1),
(2) Date: Apr. 23, 2021

(87) PCT Pub. No.: WO2020/089203
PCT Pub. Date: May 7, 2020

(65) Prior Publication Data
US 2021/0395348 A1    Dec. 23, 2021

(30) Foreign Application Priority Data
Oct. 29, 2018  (EP) .................................. 18306410

(51) Int. Cl.
| | | |
|---|---|---|
| *C07K 16/12* | (2006.01) | |
| *A61P 37/04* | (2006.01) | |
| *A61P 1/00* | (2006.01) | |
| *A61K 9/00* | (2006.01) | |
| *A61K 39/00* | (2006.01) | |

(52) U.S. Cl.
CPC ........ *C07K 16/1271* (2013.01); *A61K 9/0053* (2013.01); *A61P 1/00* (2018.01); *A61P 37/04* (2018.01); *A61K 2039/505* (2013.01); *A61K 2039/542* (2013.01); *C07K 2317/33* (2013.01)

(58) Field of Classification Search
None
See application file for complete search history.

(56) References Cited

U.S. PATENT DOCUMENTS

| | | |
|---|---|---|
| 2002/0114802 A1 | 8/2002 | Tjellstrom et al. |
| 2008/0260822 A1 | 10/2008 | Simon et al. |
| 2011/0117143 A1 | 5/2011 | Simon et al. |

FOREIGN PATENT DOCUMENTS

| | | |
|---|---|---|
| EP | 2 854 848 B1 | 10/2016 |
| WO | 2006/030883 A1 | 3/2006 |

OTHER PUBLICATIONS

Watanabe et al.; "Effects of Oral Administration of Secretory IgA on Diarrhea Associated with Severe Combined Immunodeficiency"; Pediatrics International, vol. 23, No. 2, Nov. 1, 1981, pp. 222-223.
Okai et al.; "High-affinity monoclonal IgA regulates gut microbiota and prevents colitis in mice"; Nature Microbiology, vol. 1, No. 9 Jul. 4, 2016, pp. 1-11.

*Primary Examiner* — Brian Gangle
(74) *Attorney, Agent, or Firm* — Sheppard, Mullin, Richter & Hampton LLP

(57) ABSTRACT

The invention is in the field of therapy of antibody deficiencies. Inventors demonstrate for the first time in both controls and IgA-deficient patients, systemic anti-microbiota IgG responses correlate with reduced inflammation suggesting that systemic IgG responses contribute to the gut microbiota confinement. Furthermore, SIgAd-associated inflammation is inversely correlated with systemic anti-commensal IgG responses, which may thus serve as a second line of defense. Altogether, these data suggest that systemic IgG and intestinal IgA cooperate in different body compartments to limit systemic pro-inflammatory pathways. As selective IgA deficient patients harbour elevated seric anti-commensal IgG levels, these findings suggest that in selective IgA deficiency, microbiota confinement is obtained at the price of a strong inflammatory response. Accordingly, the invention relates to a composition containing immunoglobulins A (IgA), more particularly secretory IgA, for use by oral administration in the prevention or treatment of antibody deficiencies such as SIgAd (Selective IgA deficiency) or common variable immunodeficiency (CVID) and associated inflammatory diseases.

Figure 1A:
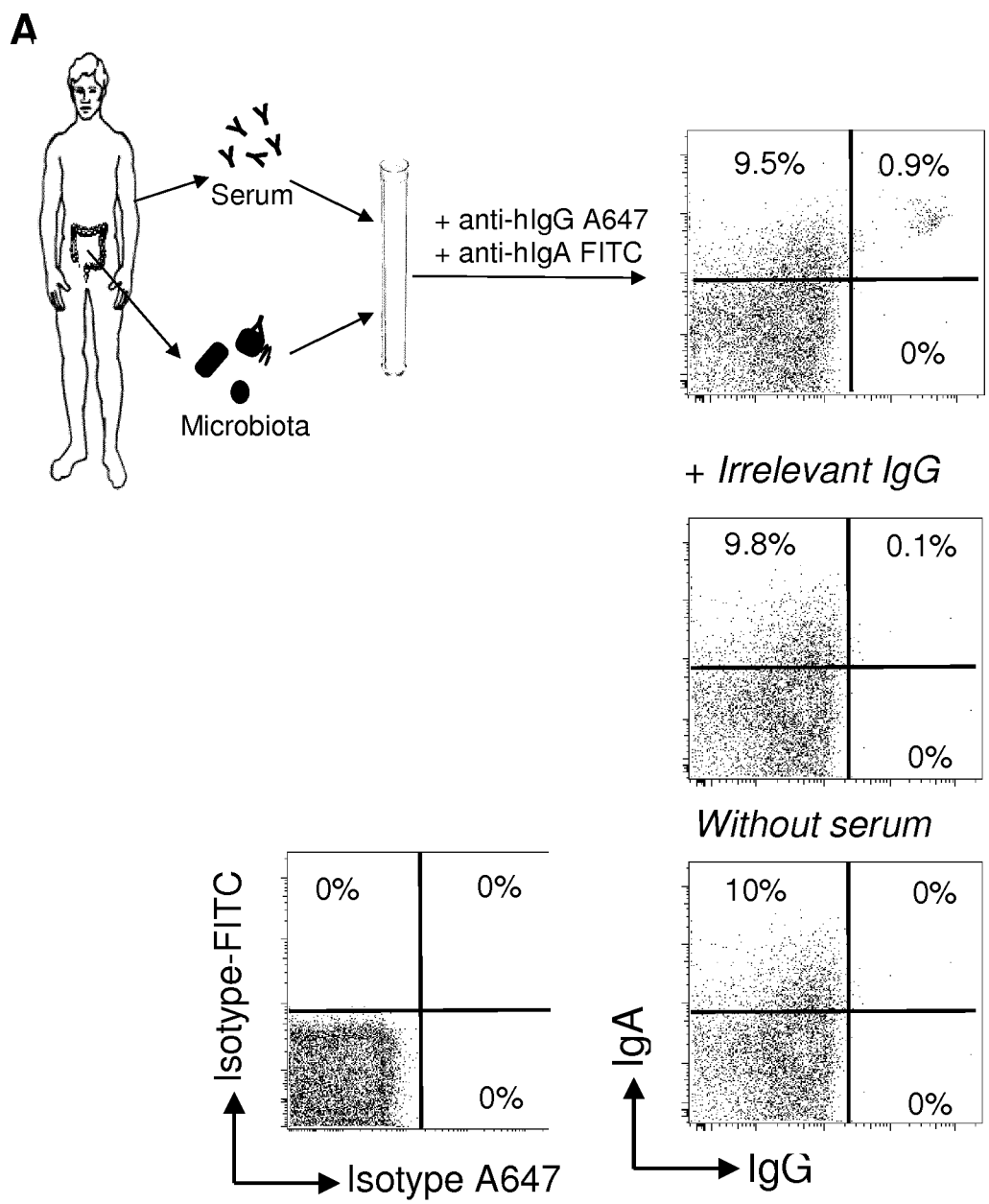

4 Claims, 13 Drawing Sheets
Specification includes a Sequence Listing.

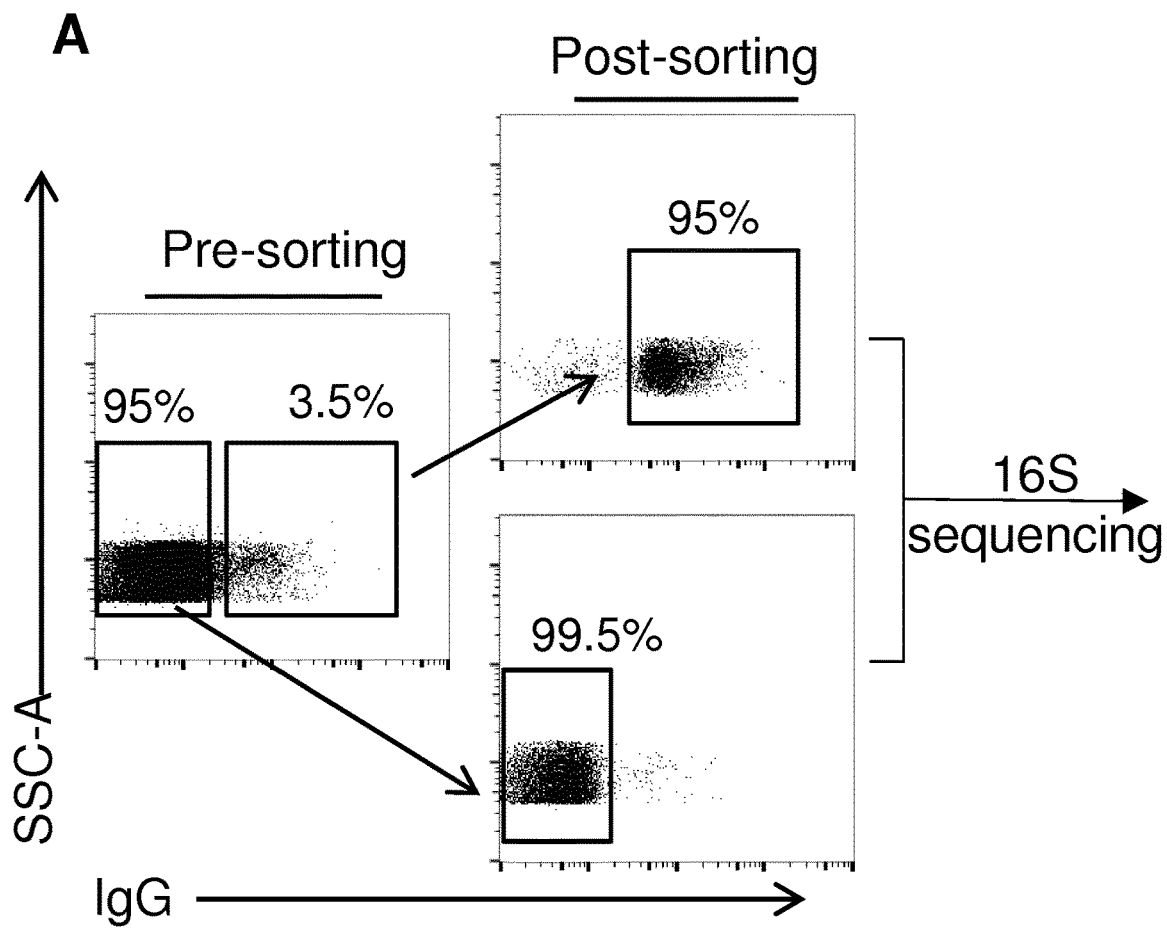
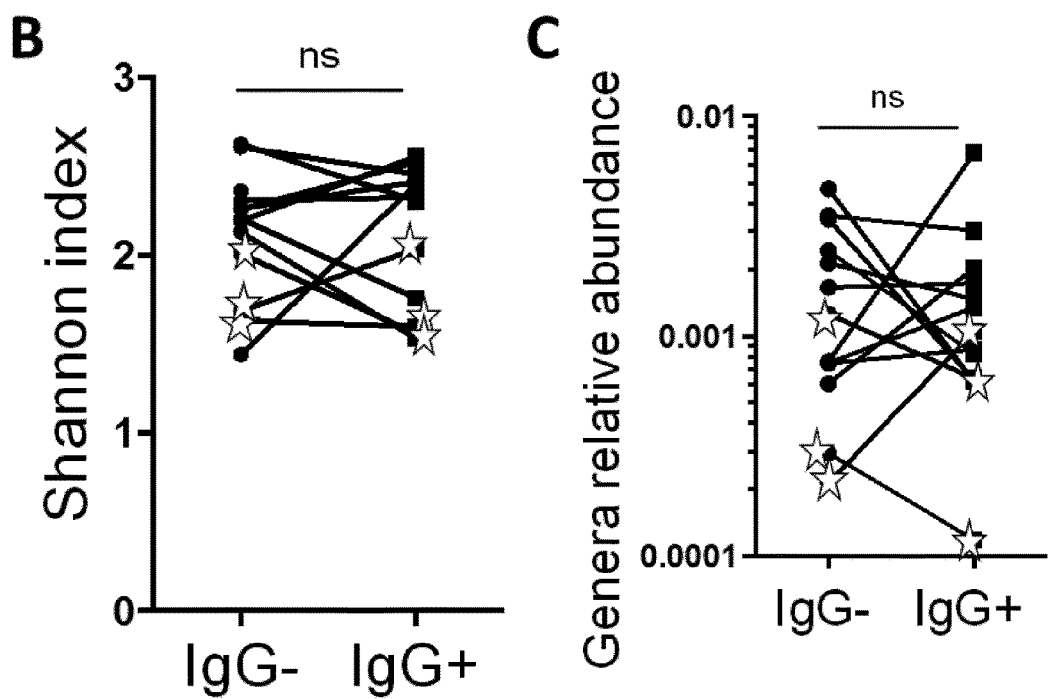
Figure 4A, 4B and 4C

SEQUENCE LISTING

```
<160> NUMBER OF SEQ ID NOS: 3

<210> SEQ ID NO 1
<211> LENGTH: 15
<212> TYPE: DNA
<213> ORGANISM: Artificial
<220> FEATURE:
<223> OTHER INFORMATION: Synthetic Primer V3fwd

<400> SEQUENCE: 1
tacggraggc agcag                                                15

<210> SEQ ID NO 2
<211> LENGTH: 23
<212> TYPE: DNA
<213> ORGANISM: Artificial
<220> FEATURE:
<223> OTHER INFORMATION: Synthetic Primer V4rev

<400> SEQUENCE: 2
atcttaccag ggtatctaat cct                                       23

<210> SEQ ID NO 3
<211> LENGTH: 18
<212> TYPE: DNA
<213> ORGANISM: Artificial
<220> FEATURE:
<223> OTHER INFORMATION: Synthetic Primers V3fwd and X926_Rev

<400> SEQUENCE: 3
ccgtcaattc mtttragt                                             18
```

COMPOSITION FOR THE TREATMENT OF ANTIBODY DEFICIENCIES

FIELD OF THE INVENTION

The invention is in the field of therapy of antibody deficiencies (primary and secondary antibody deficiencies). In particular, the invention relates to a composition containing immunoglobulins A (IgA), more particularly secretory IgA, for use by oral administration (Per os) in the prevention or treatment of primary antibody deficiencies such as SIgAd (Selective IgA deficiency) or common variable immunodeficiency (CVID), but also associated inflammatory diseases.

BACKGROUND OF THE INVENTION

Gut commensal bacteria contribute to several beneficial properties to the host. This complex community provides metabolic functions, prevents pathogen colonization and enhances immune development. A symbiotic relationship is maintained using host innate and adaptive immune responses such as antimicrobial compounds and mucus secretion, as well as IgA production[1,2]. However, the gastrointestinal tract remains an important reservoir for potential bloodstream infections that involve, among other microbes, Enterobacteriaceae, *Enterococcus* species or other Gram-negative bacilli[3,4]. The physical gut barrier, but also innate and adaptive immune mechanisms, control host-microbiota mutualism, reducing the risk of bacterial translocation and systemic immune activation. Murine models of innate immune deficiency indeed develop high seric IgG levels against gut microbiota[2]. Significant titers of IgG targeting *E. coli* were also reported either in patients with inflammatory bowel diseases or in mice lacking secretory IgA[5,6]. Nevertheless, based on recent murine studies, the notion has emerged that induction of systemic IgG responses against gut symbiotic bacteria is not necessarily a consequence of mucosal immune dysfunction or epithelial barrier leakiness. Healthy mice actively generate systemic IgG against a wide range of commensal bacteria under homeostatic conditions, which are passively transferred to the neonates through the maternal milk[7]. Serum IgG that specifically recognize symbiotic Gram-negative bacteria confer protection against systemic infections by these same bacteria. Because such IgG target a conserved antigen in commensal and pathogens, they also enhance elimination of pathogens such as *Salmonella*[8].

IgG-expressing B cells are present in human gut lamina propria during steady state conditions, and represent 3-4% of the total gut B cells. About two-third of IgG+ lamina propria antibodies react with common intestinal microbes[9]. Inflammatory bowel disease is associated with a marked increase in gut IgG+ B cells that might contribute to the observed elevated serum anti-*E. coli* IgG levels in these patients[9]. However, to which extent gut IgG+ B cells contribute to the serum IgG repertoire, remains elusive. Focusing on anti-transglutaminase 2 antibodies, a low degree of clonal relationship between serum and intestinal IgG has been shown[10]. Altogether, it remains unknown whether secretory and serum anti-bacteria antibodies have identical targets or whether digestive and systemic antibody repertoires are shaped by distinct microbial consortia.

Selective immunoglobulin A (IgA) deficiency (SIgAD) is an inherited immunodeficiency, which molecular basis remains elusive. Patients with this deficiency lack immunoglobulin A (IgA), a type of antibody that protects against infections of the mucous membranes lining the digestive, pulmonary and vaginal tracts. It is defined by an undetectable serum IgA level in the presence of normal serum levels of IgG and IgM, in persons older than 4 years. It is the most common of the primary antibody deficiencies. Although 85-90% of IgA-deficient individuals appear to be asymptomatic, this condition is associated to (i) recurrent sinopulmonary and gastrointestinal infections, (ii) inflammatory bowel disorders, (iii) autoimmune conditions and allergies (Yel, L. (2010) Journal of Clinical Immunology, 30(1), pp. 10-16 Koskinen S (1996) J Clin Immunol. 16 (3): 165-70). Moreover, occurrence of such complications increases over the years of follow up. Treatment is based on iterative antibiotics use (which is associated with complications) but no specific treatment of the underlying condition and the other complications is available. Common variable immune deficiency (CVID) is another antibody deficiency, although less prevalent (1/20000) than IgA deficiency, but much more symptomatic. In this condition, more than 95% of the patients are ill and suffer recurrent infections (95%), autoimmune diseases (30%), inflammatory bowel diseases (10-20%) and lymphoproliferation (20%). Substitutive IVIg (intravenous immunoglobulins, mainly IgG, pooled from healthy donors) are efficient to prevent airways infections but fail to control the other complications (Oksenhendler et al, Clinical infectious diseases 2008, Chapel-Hill Blood 2011).

Accordingly, there is a medical need for a specific treatment and the prevention of the complications of primary immune deficiencies, in particular SIgAd and CVID but also digestive complications such as inflammatory bowel diseases, digestive translocation and autoimmune conditions.

SUMMARY OF THE INVENTION

Inventors demonstrate for the first time the convergence of intestinal IgA and serum IgG responses toward the same microbial targets, under homeostatic conditions. Furthermore, in both controls and IgA-deficient patients, systemic anti-microbiota IgG responses correlate with reduced inflammation suggesting that systemic IgG responses contribute to the gut microbiota confinement. Finally, SIgAd-associated inflammation is inversely correlated with systemic anti-commensal IgG responses, which may thus serve as a second line of defense. Altogether, these data suggest that systemic IgG and intestinal IgA cooperate in different body compartments to limit systemic pro-inflammatory pathways. As selective IgA deficient patients harbour elevated seric anti-commensal IgG levels, these findings suggest that in selective IgA deficiency, microbiota confinement is obtained at the price of a strong inflammatory response. In conclusion, SIgAd patients, as well as CVID patients, could benefit from oral IgA supplementation. Moreover the inventors demonstrated that gut-derived IgA monoclonal antibodies are cross-reactive, in the sense that they bind to multiple commensal bacterial targets Thus, the invention relates to a composition of IgA (immunoglobulins A) for use in the treatment of antibody deficiencies, said composition being administrated orally.

In a particular embodiment, the composition comprise Secretory IgA for the treatment of primary antibody deficiencies, especially Selective IgA deficiency (SIgAd) or common variable immunodeficiency (CVID), and associated inflammatory diseases.

In another embodiment, the composition comprise Secretory IgA for the treatment of secondary antibody deficiencies, especially immune deficiencies induced by treatments (immunosuppressive or cytostatic drugs), and associated inflammatory diseases.

DETAILED DESCRIPTION OF THE INVENTION

The invention is based on the discovery that Secretory IgA is pivotal for induction of tolerance to gut microbiota and that systemic IgG and intestinal IgA cooperates in different body compartments to limit systemic pro-inflammatory pathways. These findings suggest that in selective IgA deficiency, microbiota confinement is obtained at the price of a strong inflammatory response. In conclusion, SIgAd patients and CVID patient could benefit from oral IgA supplementation.

IgA deficiency and common variable immunodeficiency (CVID) feature similar B cell differentiation arrests, it does not present the same lymphocyte subpopulation abnormalities (Litzman J, et al. Clin. Exp. Immunol. 147 (2): 249-54.). IgA-deficient patients may progress to panhypogammaglobulinemia characteristic of CVID and Selective IgA and CVID are found in the same family (Harrison's Principles of Internal Medicine, 17th edition).

IgA Composition and Method of Treatment

Based on this knowledge, the inventors propose a composition of Immunoglobulins A (IgA), which could be used in order to treat antibody deficiencies such as primary antibody deficiency or Secondary antibody deficiency and/or associated inflammatory diseases.

Thus, the invention relates to a composition of IgA (immunoglobulins A) for use in the treatment of antibody deficiencies and/or associated inflammatory diseases, said composition being administered orally.

In a specific embodiment, the composition of IgA for use according to the invention contain at least 50% of IgA.

In a specific embodiment, the composition of IgA for use according to the invention contain at least 50%, 60%, 70%, 80%, 90%, 95%, 96%, 97%, 98% or 99% of IgA.

In a specific embodiment, the composition of IgA for use according to the invention contain 100% of IgA.

In a particular embodiment, the composition of IgA for use according to the invention contain monoclonal IgA.

In a specific embodiment, the composition of IgA for use according to the invention contain at least 50% of monoclonal IgA.

In a particular embodiment, the composition of IgA for use according the invention, contain Secretory IgA.

In a specific embodiment, the composition of IgA for use according to the invention contain at least 50% of secretory IgA.

In particular embodiment, the composition of IgA for use according to the invention are not antigen-specific.

In more particular embodiment, the composition of IgA for use according to the invention are cross-reactive and bind to multiple bacterial targets.

In a particular embodiment, the antibody deficiency is selected from the list consisting of primary antibody deficiency (PAD) and secondary antibody deficiency.

As used herein, the term "primary antibody deficiencies" has its general meaning in the art and refers to a group of rare disorders characterized by an inability to produce clinically effective immunoglobulin responses. Example of primary antibody deficiencies that may be treated by methods and composition of the invention include Bruton's disease β-cell intrinsic, Good's syndrome, Hyper IgM Syndrome (HIGM), Wiskott-Aldrich syndrome (WAS) X-linked agammaglobulinemia (XLA), common variable immunodeficiency (CVID), selective IgA deficiency, specific antibody deficiency and transient hypogammaglobulinaemia of infancy (THI).

In particular embodiment, the primary antibody deficiency is SIgAd (Selective IgA deficiency) or common variable immunodeficiency (CVID).

As used herein, the term "secondary antibody deficiencies" has its general meaning in the art and are defined by a quantitative or qualitative decrease in antibodies that occur most commonly as a consequence of renal or gastrointestinal immunoglobulin loss, hematological malignancies and corticosteroid, immunosuppressive or anticonvulsant medications.

In particular embodiment the secondary antibody deficiencies is selected from the list consisting of myeloma, chronic lymphocytic leukemia (CLL), and immune deficiencies induced by treatment (immunosuppressive or cytostatic drugs).

In a specific embodiment immune deficiencies induced by treatments consist of antibody deficiencies induced by immunosuppressive drugs (used for the treatment of autoimmunity) or cytostatic drugs (used for the treatment of cancer).

The term "IgA" means "Immunoglobulin A" which exists in multiple molecular forms such as monomeric, polymeric and secretory IgA; in human it comprises two subclasses IgA1 and IgA2. In serum, IgA exists mainly in monomeric form, with a minor percentage of polymeric IgA (pIgA). In mucosal secretions (saliva, tears, colostrum, gastrointestinal fluids, nasal bronchial secretion, and urine), IgA is produced as dimers, joined by a polypeptide termed J-chain. Dimeric IgA binds to the membrane-associated polymeric Ig receptor (pIgR), and the resulting complex is transported from the baso-lateral to the apical/luminal side of mucosal epithelium. During this transport the bound IgA is released by proteolytic cleavage from the pIgR; however a portion of the pIgR, the secretory component, remains associated with dimeric IgA, forming altogether secretory IgA (SIgA). SIgA plays a major role in the immune system preventing from penetrating microorganisms the mucosal and foreign protein surfaces. It also neutralizes toxins and infectious organisms.

In a specific embodiment, the composition according the invention contain monoclonal IgA.

In a specific embodiment, the composition according to the invention, contain secretory IgA (SIgA).

In a specific embodiment, the composition according to the invention, contain monoclonal secretory IgA (SIgA).

In a specific embodiment, the composition according to the invention are cross-reactive and bind to multiple bacterial targets.

As used herein, the term "monoclonal IgA" has its general meaning in the art and refers to a preparation of IgA of single molecular composition. Monoclonal IgA displays a single binding specificity and affinity for a particular epitope. In a specific embodiment, the composition according the invention contain several different monoclonal IgA.

As used herein, the term "antigen-specific IgA composition" has its general meaning in the art and refers to a composition of IgA that recognize one specific antigen. According to the invention, the composition of IgA recognize multiple antigens. Thus, the composition of IgA for use according to the invention are not antigen-selected.

As used herein, the term "cross-reactive IgA composition" has its general meaning in the art and refers to a composition of IgA successful in binding with different antigens.

As used herein, the term "bind" or binding" in the context of the binding of an antibody to a predetermined antigen or epitope typically is a binding with a low affinity corresponding to a $K_D$ of about $10^{-6}$ M when determined by for instance surface plasmon resonance (SPR) technology in a BIAcore 3000 instrument using a soluble form of the antigen as the ligand and the antibody as the analyte. BIACORE® (GE Healthcare, Piscaataway, N.J.) is one of a variety of surface plasmon resonance assay formats that are routinely used to epitope bin panels of monoclonal antibodies. Typically, an antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein), which is not identical or closely related to the predetermined antigen. When the $K_D$ of the antibody is very low (that is, the antibody has a high affinity), then the $K_D$ with which it binds the antigen is typically at least 10,000-fold lower than its $K_D$ for a non-specific antigen. An antibody is said to essentially not bind an antigen or epitope if such binding is either not detectable (using, for example, plasmon resonance (SPR) technology in a BIAcore 3000 instrument using a soluble form of the antigen as the ligand and the antibody as the analyte), or is 100 fold, 500 fold, 1000 fold or more than 1000 fold less than the binding detected by that antibody and an antigen or epitope having a different chemical structure or amino acid sequence.

Methods for obtaining/producing such "Immunoglobulin A" are well known in the art. Examples of methods for obtaining/producing Immunoglobulin A include but are not limited to any methods described in Longet S. et al (The Journal Of Biological Chemistry VOL. 288, NO. 6, pp. 4085-4094, Feb. 8, 2013); all of which are herein incorporated by reference.

The monoclonal IgA can be made by hybridoma-based methods. Human myeloma and mouse-human heteromyeloma cell lines for the production of human monoclonal antibodies have been described. (See, e.g., Kozbor J. Immunol., 13: 3001 (1984); Brodeur et al., Monoclonal Antibody Production Techniques and Applications, pp. 51-63 (Marcel Dekker, Inc., New York, 1987); and Boerner et al., J. Immunol., 147: 86(1991).) Human antibodies generated via human B-cell hybridoma technology are also described in Li et al., Proc. Natl. Acad. Sci. USA, 103:3557-3562 (2006). Additional methods include those described, for example, in U.S. Pat. No. 7,189,826 (describing production of monoclonal human igM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005). Fully human antibodies can also be derived from phage-display libraries (as disclosed in Hoogenboom et al., 1991, J. Mol. Biol. 227:381; and Marks et al., 1991, J. Mol. Biol. 222:581). Phage display techniques mimic immune selection through the display of antibody repertoires on the surface of filamentous bacteriophage, and subsequent selection of phage by their binding to an antigen of choice. One such technique is described in PCT publication No. WO 99/10494. Monoclonal IgA described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The monoclonal IgA of the present invention may also be produced by any technique known in the art, such as, without limitation, any chemical, biological, genetic or enzymatic technique, either alone or in combination. For example, knowing the amino acid sequence of the desired sequence, one skilled in the art can readily produce said IgA, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, monoclonal IgA of the present invention can be synthesized by recombinant DNA techniques well-known in the art. For example, antibodies can be obtained as DNA expression products after incorporation of DNA sequences encoding the monoclonal IgA into expression vectors and introduction of such vectors into suitable eukaryotic or prokaryotic hosts that will express the desired monoclonal IgA, from which they can be later isolated using well-known techniques.

Briefly, Secretory component of IgA can be obtained from human colostrum or produced in a recombinant form. pIgA (polymeric IgA) can be purified from human plasma. The production of secretory IgA is performed by mixing secretory component and pIgA in PBS and the produced secretory IgA is functional and stable (Longet S. et al (2013)) demonstrates that. The process can be scaled to industrial scale. Industrial scale is presently 10000 L for IVIG (Intravenous immunoglobulins) production, which would allow production of 500 grams of pIgA. The recombinant secretory component of IgA is expressed in CHO cells and could at industrial scale produce the amounts required for 500 grams of pIgA (125 grams of Secretory component).

Recombinant Secretory IgA could also be produced in plants that could be directly used as food supplements. Recombinant Secretory IgA should also be considered produced by modified probiotic bacterial strains. Such methods for obtaining/producing recombinant immunoglobulin in plants or bacterial strains are well known in the art (Production of antibodies in transgenic plants. A Hiatt, R Cafferkey, K Bowdish—Nature 342, pages 76-78, 1989)

The term "SIgAd" means "Selective IgA deficiency". SIgAD, using 0.05 g/l of serum IgA as the upper limit for diagnosis in adults and a concomitant lack of secretory IgA, is the most common form of primary immunodeficiency (PID) in the western world and affects approximately 1/600 individuals in 2000's (Clin Exp Immunol 1997; 159:6236 41.). However, there is a marked variability in the prevalence in different ethnic groups (Hammarström L et al. Primary immunodeficiency diseases, a molecular and genetic approach. Oxford: Oxford University Press, 1999: 250 62.), with a lower frequency in Japanese (1/18000) and Chinese (1/4000), suggesting a genetic basis for the disorder. The term 'selective IgAD' should be reserved for those individuals who do not have identifiable disorders which are known to be associated with low IgA levels. However, in many cases a simultaneous change in the IgG subclass pattern is seen with a lack of specific anti-polysaccharide antibodies of the IgG2 subclass (Hammarström L, et al. Immunology 1985; 54:821 6) or a total lack of serum IgG2 (Oxelius V et al. N Engl J Med 1981; 304:1476 7.), IgG4 and IgE (Hammarström L, et al Monogr Allergy 1986; 20:234 5.), reflecting a relative or absolute block in switching to genes downstream of the G1.

The term "CVID" means "common variable immunodeficiency" is an immune disorder characterized by recurrent infections and low antibody levels, specifically in immunoglobulin (Ig) types IgG, IgM and IgA. Generally symptoms include high susceptibility to foreign invaders, chronic lung disease, inflammation and infection of the gastrointestinal tract. However, symptoms vary greatly between people. CVID is a lifelong disease. CVID affects about 1/25000 Caucasians, the patients having a marked reduction in serum levels of both IgG (usually <3 g/l) and IgA (<0.05 g/l); IgM is also reduced in about half the patients (<0.3 g/l) (Clin Exp Immunol 1997; 159:6236 41.). Symptoms of recurring infection can start at any time of life, but there are peaks of onset during 1-5 and 16-20 years of age (Hermaszewski R A et al Quart J Med 1993; 86:31 42), with equal distribution between the sexes. The condition is clinically more complex than X-linked agammaglobulinaemia (XLA), with patients being prone to chronic inflammatory and autoimmune complications (Cunningham-Rundles C et al. J Clin Immunol 1999; 92:34 48.).

The term "associated inflammatory diseases" in the context of the present invention means immune suppressive disease selected from the list induced by pathogens or drugs, such as sepsis, autoimmune disease (like graft versus host disease) and/or malabsorption and/or inflammatory gut disease (like IBD).

In a specific embodiment associated inflammatory diseases is inflammatory gut disease such as Inflammatory Bowel Diseases (IBD) or Irritable Bowel Syndrome (IBS).

As used herein, the term "inflammatory bowel diseases (IBD)" is a group of inflammatory diseases of the colon and small intestine. The major types of IBD are Crohn's disease, ulcerative colitis Celiac disease, and pouchitis.

As used herein, the term "Irritable Bowel Syndrome (IBS)" is a term for a variety of pathological conditions causing discomfort in the gastro-intestinal tract. It is a functional bowel disorder characterized by chronic abdominal pain, discomfort, bloating, and alteration of bowel habits in the absence of any organic cause. It also includes some forms of food-related visceral hypersensitivity, such as Gluten hypersensitivity.

Another object of the invention is a method for treating antibody deficiency disorders such as primary antibody deficiencies like Selective IgA deficiency (SIgAd) and as common variable immunodeficiency (CVID), comprising administering to a subject in need thereof a therapeutically effective amount of a composition of Immunoglobulin A (IgA) according to the invention as disclosed above.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.])

By a "therapeutically effective amount" is meant a sufficient amount of compound to treat and/or to prevent antibody deficiency disorders such as primary antibody deficiencies like Selective IgA deficiency (SIgAd) or common variable immunodeficiency (CVID), and inflammatory associated diseases.

It will be understood that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed, the age, body weight, general health, sex and diet of the patient; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved.

In the case of Selective IgA deficiency (SIgAd) and as common variable immunodeficiency (CVID), the daily effective dose level of IgA composition could be 0.5 to 5 grams/day, considering daily production levels of IgA in healthy individuals (M. E. Conley, D. L. Delacroix, Intravascular and mucosal immunoglobulin A: Two separate but related systems of immune defense? Ann. Intern. Med. 106, 892-899 (1987).).

Pharmaceutical Composition

The IgA composition of the present invention, together with one or more conventional adjuvants, carriers, or diluents may be placed into the form of pharmaceutical compositions and unit dosages.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The pharmaceutical compositions and unit dosage forms may comprise conventional ingredients in conventional proportions, with or without additional active compounds or principles, and the unit dosage forms may contain any suitable effective amount of the active ingredients commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal administration; or in the form of sterile injectable solutions for parenteral uses. Formulations containing about one (1) milligram of active ingredient or, more broadly, about 0.01 to about one hundred (100) milligrams, per tablet, are accordingly suitable representative unit dosage forms.

The IgA composition of the present invention may be formulated in a wide variety of oral administration dosage forms. The pharmaceutical compositions and dosage forms may comprise compounds of the present invention or pharmaceutically acceptable salts thereof as the active component. The pharmaceutically acceptable carriers may be either solid or liquid. Solid form preparations include powders, tablets, pulls, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid, which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch gelatin, tragacanth, methylcellulose sodium carboxymethylcellulose, a low melting wax, cocoa butter, and the like.

The term "preparation" is intended to include the formulation of the active compound with an encapsulating material as carrier, providing a capsule in which the active component, with or without carriers, is surrounded by a carrier, which is in association with it. Similarly, cachets and lozenges are included. Tablets, powders, capsules, pulls, cachets, and lozenges may be as solid forms suitable for oral administration.

IgA composition might be orally delivered through a carrier system allowing colon delivery. Colon-targeted drug delivery systems (CDDS) include several formulations and sometimes combination of variant approaches. The colon contains many species of anaerobic bacteria fermenting polymers such as derivatives of guar gum (Include REF roos AA Biomacromolecules 2008; 9(8):2104-10), azo-aromatic polymers. These polymers can be used to coat the drug (here IgA) permitting drug release in the colon. Another approach includes embedding the drug in polymer matrix to trap it. Matrix-based systems, using for instance natural polymer called Assam Bora rice starch, exhibit a sustained release of the drug in colonic environment. IgA might be embedded into bioadhesive microsphere covered with polymers such as polycarbophils, polyurethanes and polyethylene oxide. Bioadhesive systems allow the tablets to remain in contact within enterocytes. Polysaccharides are another option for CDDS. Cellular derivatives, pectin, chitosan, chondroitin sulfate can be combined to optimized the drug release. Incorporating IgA in a pH-sensitive polymers might protect IgA from the acidic pH of the stomach and duodenum. Methacrylic-acid based polymer is a common pH-sensitive polymer. Inclure REF Sandolo C, Péchiné S, Le Monnier A, Hoys S, Janoir C, Coviello T, et al. Encapsulation of Cwp84 into pectin beads for oral vaccination against *Clostridium difficile*. Eur J Pharm Biopharm Off J Arbeitsgemeinschaft Pharm Verfahrenstechnik EV. 2011; 79:566-73. ET Amidon S. AAPS PharmSciTech 2015, 16(4) August ET Ramteke Advanced Pharmaceutical Bulletin 2014; 4(2)167-177.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavours, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavours, stabilizers, buffers, artificial and natural sweeteners, dispersants, thickeners, solubilising agents, and the like.

The dosing is selected by the skilled person so that an anti-inflammation effect is achieved, and depends on the route of administration and the dosage form that is used. Total daily dose of a peptide administered to a subject in single or divided doses may be in amounts, for example, of from about 0.001 to about 100 mg/kg body weight daily and preferably 0.01 to 10 mg/kg/day. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

The invention will be further illustrated by the following figures and examples. However, these examples and figures should not be interpreted in any way as limiting the scope of the present invention.

FIGURES

FIG. 1: Systemic IgG and secretory IgA recognize a common spectrum of commensals.

A. Representative flow cytometry dot plot showing from bottom to top isotype control, endogenous secretory IgA (without serum), human IgG anti-TNF (10 µg/ml; irrelevant IgG) and autologous systemic IgG (10 µg/ml) to fecal microbiota in a healthy donor.

B. Flow cytometry analysis of the fraction of fecal microbiota bound by either secretory IgA, seric IgG or both in healthy donors (n=30). Median values are indicated and subgroups are compared with a non-parametric Mann-Whitney test.

FIG. 2: Systemic IgG bind a broad spectrum of commensals

A. Flow cytometry analysis of serum IgG binding to cultivated bacterial strains. Grey histograms represent isotype controls and dark lines anti-IgG staining.

B. Flow cytometry analysis of serum IgG binding levels to 8 different bacterial strains in healthy donors (n=30). Blue strains (left) are typically poorly coated by secretory IgA from healthy individuals while pink strains (right) are representative of typical IgA targets[15]. Results are presented as A Median Fluorescence Intensity (MFI) i.e.: IgG=MFI IgG serum—MFI IgG negative control. Red bars show medians. Kruskal-wallis test was used to calculate p-value.

C. Representative immunoblotting of *Escherichia coli* lysates probed with five different healthy human serums, with a normalized IgA and IgG levels. Ponceau staining indicates total amounts of bacteria lysates loaded. IgA and IgG binding were assessed by an HRP conjugated secondary antibody.

FIG. 3: IgA deficient patients harbour private anti-commensal IgG responses.

A. Flow cytometry analysis of fecal microbiota bound by autologous seric IgG in healthy donors (n=30) and IgA deficient patients (n=15). Red bars represent medians. P-value was calculated by Mann-Whitney test.

B. Representative flow cytometry analysis of autologous seric IgG binding (left) or polyclonal IgG derived from pooled serum of healthy donors binding (right) to fecal microbiota. In a healthy donor (top) and in an IgA deficient patient (bottom).

C. Flow cytometry analysis of the IgG-bound fecal microbiota with IgG from autologous serum or polyvalent IgG in healthy donors (n=30) and IgA deficient patients (n=15). P-values were calculated by Wilcoxon-paired test.

D. Flow cytometry detection of IgG on IgA deficient microbiota (n=9), following incubation with autologous serum or heterologous serum from another, randomly picked, IgA deficient individual. P-value was calculated by Wilcoxon-paired test.

FIG. 4: Private IgG anti-microbial signatures.

A. Sorting strategy of IgG-bound and IgG-unbound microbiota in 10 healthy donors and 3 IgA deficient patients. Composition of sorted subsets was next analysed by 16S rRNA sequencing.

B. Genera diversity in IgG+ and IgG− sorted fractions calculated by Shannon index. Dark symbols correspond to healthy donors, star symbols to IgA deficient patients.

C. Median relative abundance of genera in IgG+ and IgG− sorted fractions. Dark symbols correspond to healthy donors, star symbols to IgA deficient patients.

FIG. 5: Microbiota specific IgG and inflammation

A. Percentage of serum IgG-bound microbiota correlated with sCD14 levels in autologous serum of healthy donors (triangles) and SIgAd patients (dark points). Spearman coefficient (r) and p-value (p) are indicated.

B. Flow cytometry analysis of IgG-bound microbiota following IVIG exposure in healthy donors and CVID patients.

C. sCD14 levels measured by ELISA in plasmas of healthy donors and CVID patients.

D. Seric IL-6 levels measured by Simoa technology in plasmas of healthy donors and CVID patients.

E. Flow cytometry analysis of CD4+CD45RA-PD-1+ lymphocytes in peripheral blood mononuclear cells of healthy donors and CVID patients. Percentage among CD4+ T cells is presented.

For all dot plots, black lines represent medians. Mann-Whitney test was used to calculate p-values (*p<0.05, ***p<0.001)

Figure 6:
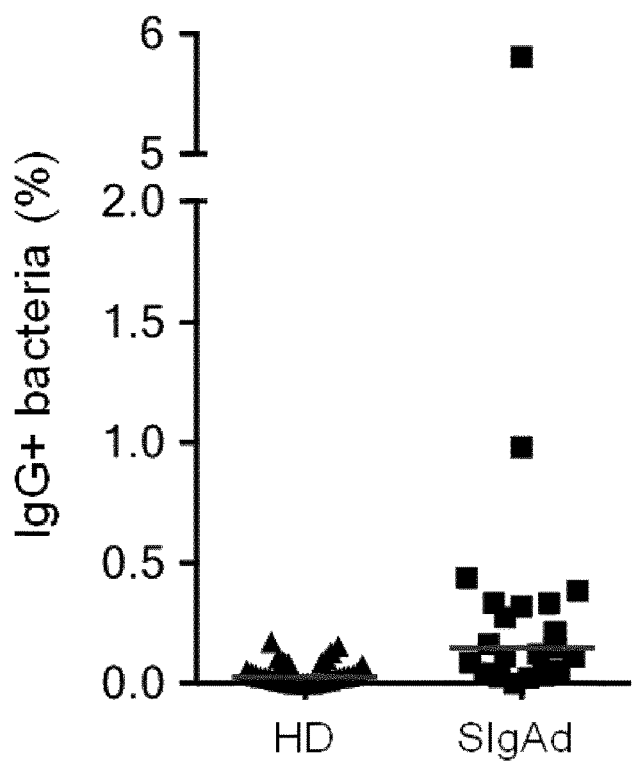

FIG. 6: In vivo intestinal IgG binding to gut microbiota

Flow cytometry analysis of the fraction of fecal microbiota bound by intestinal IgG in healthy donors (HD; n=30) and selective IgA deficient patients (SIgAd; n=15). Pink bars represent medians.

FIG. 7: Anti-commensals IgG react mostly in a Fab-dependent manner

A-B. Flow cytometry analysis of 30 healthy (A) and 15 IgA deficient (B) fecal microbiota samples incubated with seric IgG or human IgG anti-TNF.

C. Flow cytometry analysis of 10 IgA deficient fecal microbiota samples incubated with heterologous seric IgG or human IgG anti-TNF.

Wilcoxon-paired test was used to calculate p-values. p<0.01;*p<0.001; ****p<0.0001

FIG. 8: Human monoclonal IgA target highly diverse commensal bacteria.

A. mAb+ and mAb− fractions of IgA-free gut microbiota were sorted by flow cytometry and their composition was analysed by 16S rRNA sequencing.

B-C. Relative abundance of phyla in whole microbiota (input) and mAb+ fractions. Microbiota #A is IgA-free, while Microbiota #B is IgA- and IgG-free.

EXAMPLE 1

Material & Methods

Human Samples

Fresh stool and blood samples were simultaneously collected from n=30 healthy donors, n=15 selective IgA deficiency and n=10 common variable immunodeficiency patients.

Healthy donors were recruited among laboratory staff and relatives. Patients followed for clinical manifestations associated with antibody deficiencies were recruited from two French clinical immunology referral centers (Department of Clinical Immunology at Saint Louis hospital and Department of Internal Medecine at Pitié-Salpêtrière hospital, Paris). Patient's inclusion criteria were (i) undetectable seric IgA levels (<0.07 mg/mL) in at least three previous samples in the past year (ii) either selective IgA deficiency (n=15 selective IgA deficient patients), or associated with IgG and/or IgM deficiency integrating a global antibody production defect (n=10 CVID patients). Clinical and biological data were collected at inclusion time.

Surgical samples from histologically normal intestine were obtained from twelve donors undergoing gastric bypass or tumorectomy at Pitié-Salpêtrière hospital, Paris.

Oral and written consent were obtained from patients and healthy donors before inclusion in the study.

PBMC and Plasma 30 mL of blood were collected in ACD tubes (BD Vacutainer®) and PBMC were isolated by density gradient procedure (Ficoll 400, Eurobio, Les Ulis, France) and then stored in liquid nitrogen after soft freezing in isopropanol. Supernatants were collected as plasma and immediately stored at −80° C.

Stool Collection and Whole Microbiota Purification

Stool were collected immediately after emission in a container allowing anaerobic bacteria preservation (Anaerocult band, Merck, Darmstadt, Germany), aliquoted in a $CO_2$-rich 02-low atmosphere and stored at −80° C. Fecal microbiota were extracted by gradient purification in anaerobic conditions (Freter chamber) as previously described[37].

Briefly, thawed feces were diluted in 1×-PBS (Eurobio), 0,03% w/v sodium deoxycholate (NaDC), 60% w/v Nycodenz (Sigma-aldrich, St Louis, USA) and loaded on a continuous density gradient obtained by a freezing-thawing cycle of a Nycodenz solution. Fecal bacteria were obtained after ultracentrifugation (14567×g, 45 min, +4° C.) (Beckman Coulter ultracentrifuge, swinging rotor SW28) and washed three times in 1×-PBS (Eurobio), 0,03% w/v sodium NaDC. The final pellet was diluted in 1×PBS-10% Glycerol, immediately frozen in liquid nitrogen and then stored at −80° C.

Bacterial Flow Cytometry

Specific seric antibodies levels against purified microbiota or cultivable strains were assessed by a flow cytometry assay as previously described[11]. Briefly, $10^7$ bacteria (purified microbiota or cultivable strains) were fixed in a solution of 4% paraformaldehyde and simultaneously stained with a cell proliferation dye (eFluor 450, eBiosciences, CA, USA). After washing with 1 mL of a 1×-PBS solution, cells were resuspended to a final concentration of $4 \cdot 10^8$ bacteria/mL in a 1×-PBS, 2% w/v BSA, 0.02% w/v Sodium azide solution. Then $10^7$ bacteria were incubated in a 96-V bottom well plate with a 10 μg/mL IgG solution (from either human serum or pooled human IgG Hizentra®-CSL Behring France or human anti-TNF Remicade®—MSD France) per condition. Immune complexes were washed twice with a 1×-PBS, 2% w/v BSA, 0.02% w/v Sodium azide (200 μL/well, 4000×g, 10 minutes, +4° C.) and then incubated with secondary conjugated antibodies, either isotype controls mix or goat anti-human IgA-FITC and goat anti-human IgG-A647 (Jackson Immunoresearch Laboratories, West Grove, USA). Acquisition of the cells events was performed on a FACS CANTO II flow cytometer (Becton Dickinson) after washing and analysis was performed with Flow-Jo software (Treestar, Ashland, USA). Medians of fluorescence were used to measure the seric IgG response levels against the cultivable strains. Intestinal IgA binding was quantified by the same assay without incubation with seric immunoglobulins. Results are expressed as median, minimum and maximum percentages throughout the manuscript.

Cytokines Quantification

IL-6 and IL-10 were measured in the serum using a 3-step digital assay relying on Single Molecule Array (Simoa) technology HD-1 Analyzer (Quanterix Corporation, Lexington, USA). Working dilutions were ¼ for all sera in working volumes of 25 μL. Lower limit of quantification for IL-6 and IL-10 are respectively of 0.01, 0.021 pg/mL.

Soluble CD14 Quantification

Soluble CD14 was quantified in plasma (400-fold dilution) by ELISA (Quantikine® ELISA kit, R&D, Minneapolis, USA). Experimental procedure followed the manufacturer's recommendations. Lower limit of quantification for soluble CD14 is of 6 pg/mL.

Peripheral Blood Mononuclear Cell Phenotyping

T cell phenotyping was performed using a combination of the following antibodies: CD3-H500, CCR7-PE-Cy7, CD4-APC-Cy7 (BD Biosciences), CD45RA-PercP Cy5.5 (e-Bioscience), CD8-A405 (Invitrogen), CD279-APC (BioLegend). Acquisition of cells events was performed using a FACS CANTO II flow cytometer (Becton Dickinson) and analysis was performed using the Flow-Jo software (Treestar).

Intestinal B Cells Phenotyping

Lamina propria was digested by collagenase A (Roche) in RPMI (Life Technologies) for 30 minutes at 37° C. Lymphocytes were purified by centrifugation over Ficoll 400 (Eurobio) and stained with the following antibodies: anti-CD45 APC-H7, anti-CD19 BV421, anti-IgD FITC, anti-CD27 PE-Cy7 (all purchased from BD Biosciences), and anti-IgA PE (Jackson Immunoresearch), or anti-IgG1 PE, anti-IgG2 AF488, anti-IgG3 A647 (Southern Biotech). Dead cells were excluded with LIVE/DEAD™ Fixable Aqua Dead Cell Stain Kit (Invitrogen). Acquisition of cells events was performed using a FACS CANTO II flow cytometer (Becton Dickinson) and analysis was performed using the Flow-Jo software (Treestar).

Analysis of IgG-Coated Bacteria

Purified microbiota ($10^9$/condition) was washed in 1×-PBS and stained with isotype control (A647-conjugated Goat IgG, Jackson Immunoresearch Laboratories) as a negative control or anti-human IgG-A647 (Jackson Immunoresearch Laboratories). Acquisition and sorting were performed on a 2 lasers—2 ways Fluorescent—activated cell sorter (S3 cell sorter, Bio-Rad Laboratories, California, USA). $10^6$ bacteria per fraction were collected and immediately stored at −80° C. as dry pellets. Purity for both fractions was systematically verified after sorting with a minimum rate of 80%. Genomic DNA was extracted and the V3-V4 region of the 16S rRNA gene was amplified by semi-nested PCR. Primers V3fwd (+357): 5' TACG-GRAGGCAGCAG 3' (SEQ ID N° 1) and V4rev (+857): 5' ATCTTACCAGGGTATCTAATCCT 3' (SEQ ID N° 2) were used during the first round of PCR (10 cycles). Primers V3fwd and X926_Rev (+926) 5' CCGTCAATTCMTT-TRAGT 3' (SEQ ID N° 3) were used in the second PCR round (40 cycles). Polymerase chain reaction amplicon libraries were sequenced using a MiSeq Illumina platform (Genotoul, Toulouse, France). The open source software package Quantitative Insights Into Microbial Ecology (QIIME)[38] was used to analysed sequences with the following criteria: (i) minimum and maximum read length of 250 bp and 500 bp respectively, (ii) no ambiguous base calls, (iii) no homopolymeric runs longer than 8 bp and (iv) minimum average Phred score >27 within a sliding window of 50 bp. Sequences were aligned with NAST against the GreenGenes reference core alignment set (available in QIIME as core set aligned.fasta.imputed) using the 'align seqs.py' script in QIIME. Sequences that did not cover this region at a percent identity >75% were removed. Operational taxonomic units were picked at a threshold of 97% similarity using cd-hit from 'pick_otus.py' script in QUIIME. Picking workflow in QUIIME with the cd-hit clustering method currently involves collapsing identical reads using the longest sequence-first list removal algorithm, picking OTU and subsequently inflating the identical reads to recapture abundance information about the initial sequences. Singletons were removed, as only OTU that were present at the level of at least two reads in more than one sample were retained (9413±5253 sequences per sample). The most abundant member of each OTU was selected through the 'pick_rep_set.py' script as the representative sequence. The resulting OTU representative sequences were assigned to different taxonomic levels (from phylum to genus) using the GreenGenes database (release August 2012), with consensus annotation from the Ribosomal Database Project naïve Bayesian classifier [RDP 10 database, version 6[39]. To confirm the annotation, OTU representative sequences were then searched against the RDP database, using the online program seqmatch (http://rdp.cme.msu.edu/seqmatch/seqmatch_intro.jsp) and a threshold setting of 90% to assign a genus to each sequence.

Immunoblotting $10^8$ CFU of wild type *Escherichia coli* were freezed (−80° C.) and thawed (37° C.) three times in 30 μL of lysis buffer (50 mM Tris-HCL, 8M urea). Lysis efficiency was verified by Gram staining. Proteins were separated using 4%-20% polyacrylamide gel electrophoresis (Mini-PROTEAN TGX Stain-Free Precast Gels; Bio-Rad) in reducing conditions (dithiothreitol DTT and sodium dodecyl sulfate SDS, Bio-Rad) and transferred to nitrocellulose. Membranes were incubated with 10 µg/ml of human seric IgG or IgA of different healthy donors. Human IgG were detected with horseradish peroxidase-conjugated goat anti-human IgG used at 1:50,000 or goat anti-human IgG used at 1:20,000 followed by enhanced chemi-luminescence revealing reaction (Clarity™ Western ECL, Bio-Rad). Human IgA were detected with horseradish peroxidase-conjugated goat anti-human IgA used at 1:20 000 (Bethyl Laboratories). All incubations were in 1×-PBS with 5% non fat milk and washing steps in 1×-PBS with 0.1% Tween.

IgG Gene Expression Analysis

Total RNA of jejunal lamina propria fraction and PBMC were extracted with the RNeasy Mini kit (QIAGEN). cDNAs were synthesized from and prepared with M-MLV reverse transcriptase (Promega). SYBR green primers were designed by manufacturer (Roche) and used for qRT-PCR using the 7300 real time PCR system (Applied Biosystem). Data were normalized to ribosomal 18S RNA.

Results

1/ Convergence of Intestinal IgA and Serum IgG Toward the Same Bacterial Cells

Figure 1B:
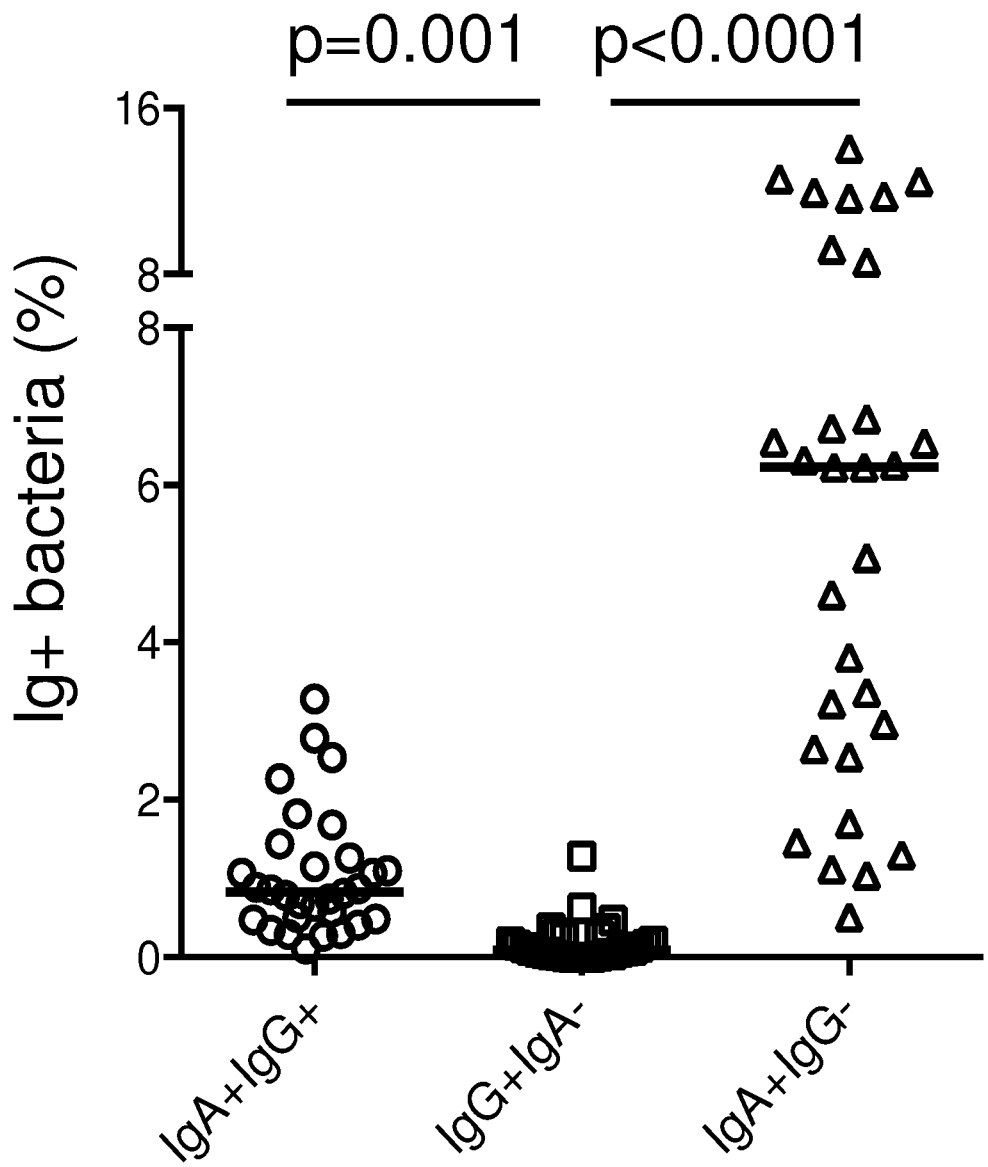

To determine the level of humoral systemic response against fecal microbiota, we have elaborated a flow cytometric assay derived from a previously reported technology[11]. This protocol allows to probe concomitantly IgA and IgG microbiota coating. We found that approximately 8% of the fecal microbiota is targeted by secretory IgA (median [min–max]%; 8[0.8–26.7]%; n=30) in healthy donors, in concordance with previous reports[12]. As shown, the proportion of bacteria in vivo bound by secretory IgA in human feces is highly variable between healthy individuals (FIG. 1B). IgG-bound bacteria are virtually absent from healthy human feces (median [min–max]%; 0.03[0–0.16]%; n=30; FIGS. 6 and 1A), in agreement with the lack of IgG transport to the intestinal lumen. In healthy donors, seric IgG bound a median rate of 1.1% of fecal bacteria (median [min–max]%; 1.1[0.2–3.2]%; FIG. 1B). Surprisingly, seric IgG targeted exclusively secretory IgA bound bacteria (FIG. 1A). Conversely, all IgA-coated bacteria (IgA+ bacteria) were not targeted by seric IgG. Of note, an irrelevant human monoclonal IgG (chimeric anti-human TNF containing a human Fc IgG fraction) exhibits markedly reduced binding to IgA+ bacteria, compared to serum IgG (FIGS. 1A, 7A, 7B and 7C), demonstrating that IgG binding to IgA-coated bacteria is mostly Fab-mediated.

Figure 2A:
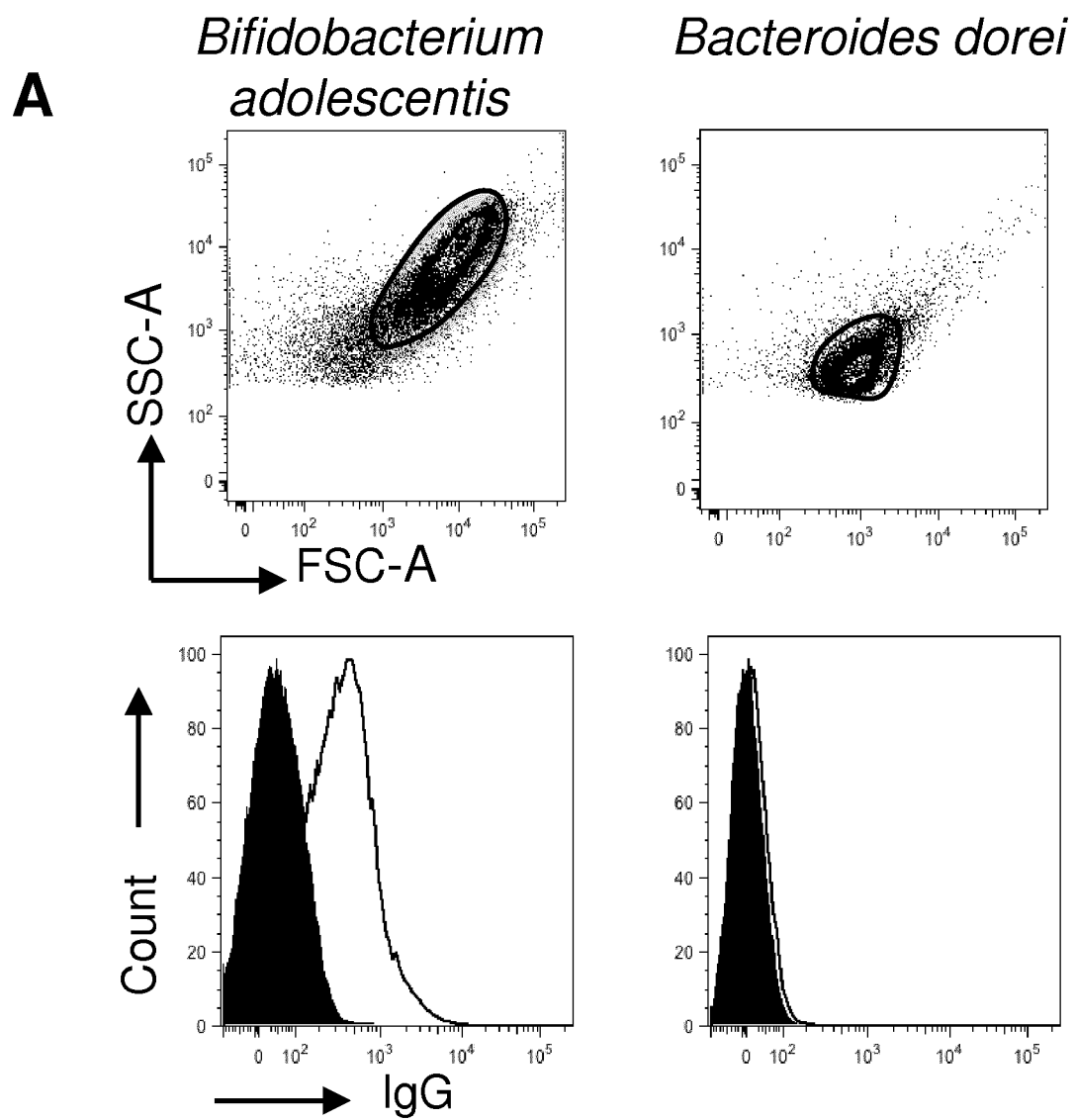
Figure 2B:
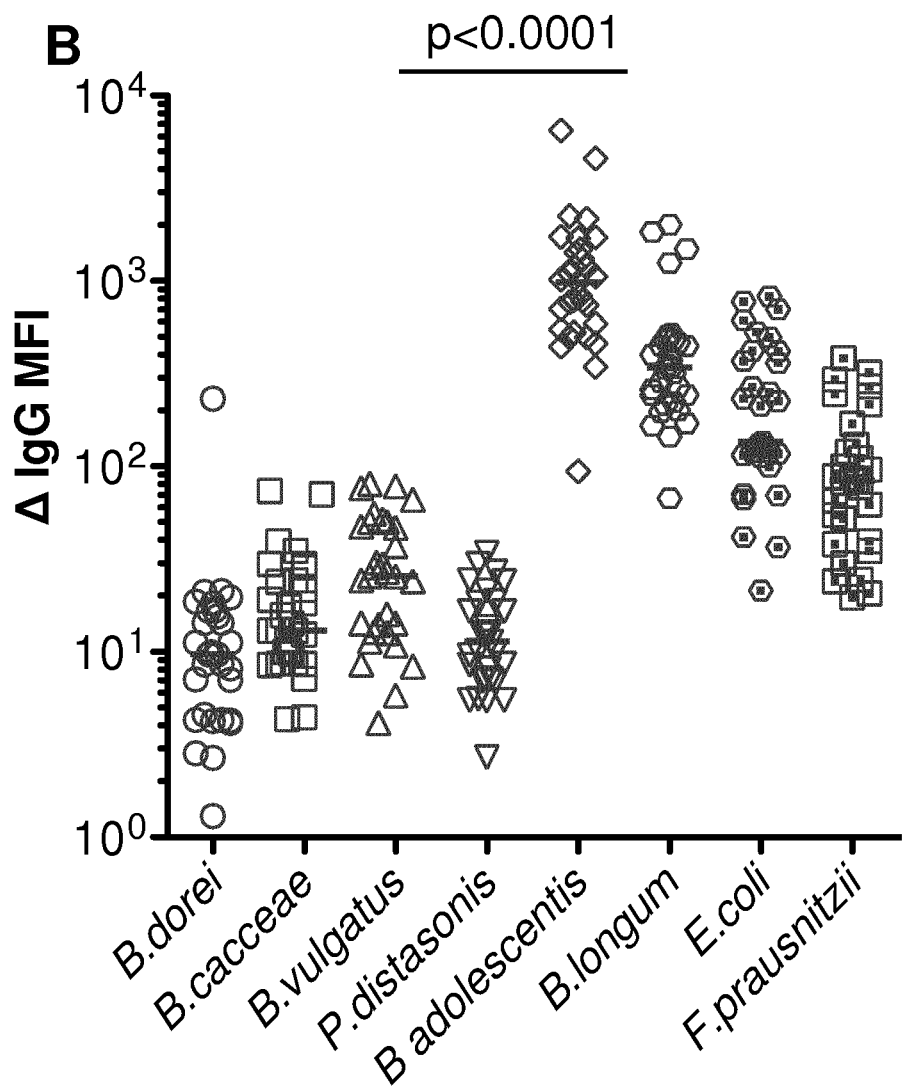

To confirm that systemic IgG binding is directed against IgA-bound bacteria, we evaluated in vitro serum IgG binding to cultivable bacterial strains. We selected four bacterial strains that were not preferentially bound by IgA in human feces and four others that were previously defined as classical IgA targets in vivo[12-14] As shown in FIG. 2, IgG from healthy individuals (n=30) bind much more significantly *Bifidobacterium longum, Bifidobacterium adolescentis, Faecalibacterium prausnitzii* and *Escherichia coli*, known to be particularly enriched in the IgA-coated fraction of healthy individuals, than three different strains of *Bacteroides* sp. and *Parabacteroides distasonis*, known to be particularly enriched in the IgA-uncoated fraction of the fecal microbiota (FIG. 2A-B). The majority of anti-commensal IgG antibodies are of the IgG2b and IgG3 isotypes in mice. Using isotype-specific secondary antibodies we detected minimal IgG1 binding, but high seric IgG2 reactivity, to *Bifidobacterium adolescentis, Bifidobacterium longum* and *Escherichia coli*, suggesting that IgG2 is involved in commensals targeting in humans (data not shown).

Since anti-commensal IgG might possibly be triggered during mucosal immune responses, we characterized lamina propria B cells and detected the presence of IgG2+ B cells throughout the intestine (data not shown). Of note, IgG transcripts are more abundant in LP tissue that in PBMCs, as measured by qPCR (data not shown).

These results demonstrate that human IgG recognize a wide range of commensal under homeostatic conditions. Systemic humoral immunity (notably IgG2) converges with mucosal immunity to bind the surface of commensals.

2/ Inter-Individual Variability and Non Overlapping Anti-Commensal IgA and IgG Molecular Targets.

Figure 2C:
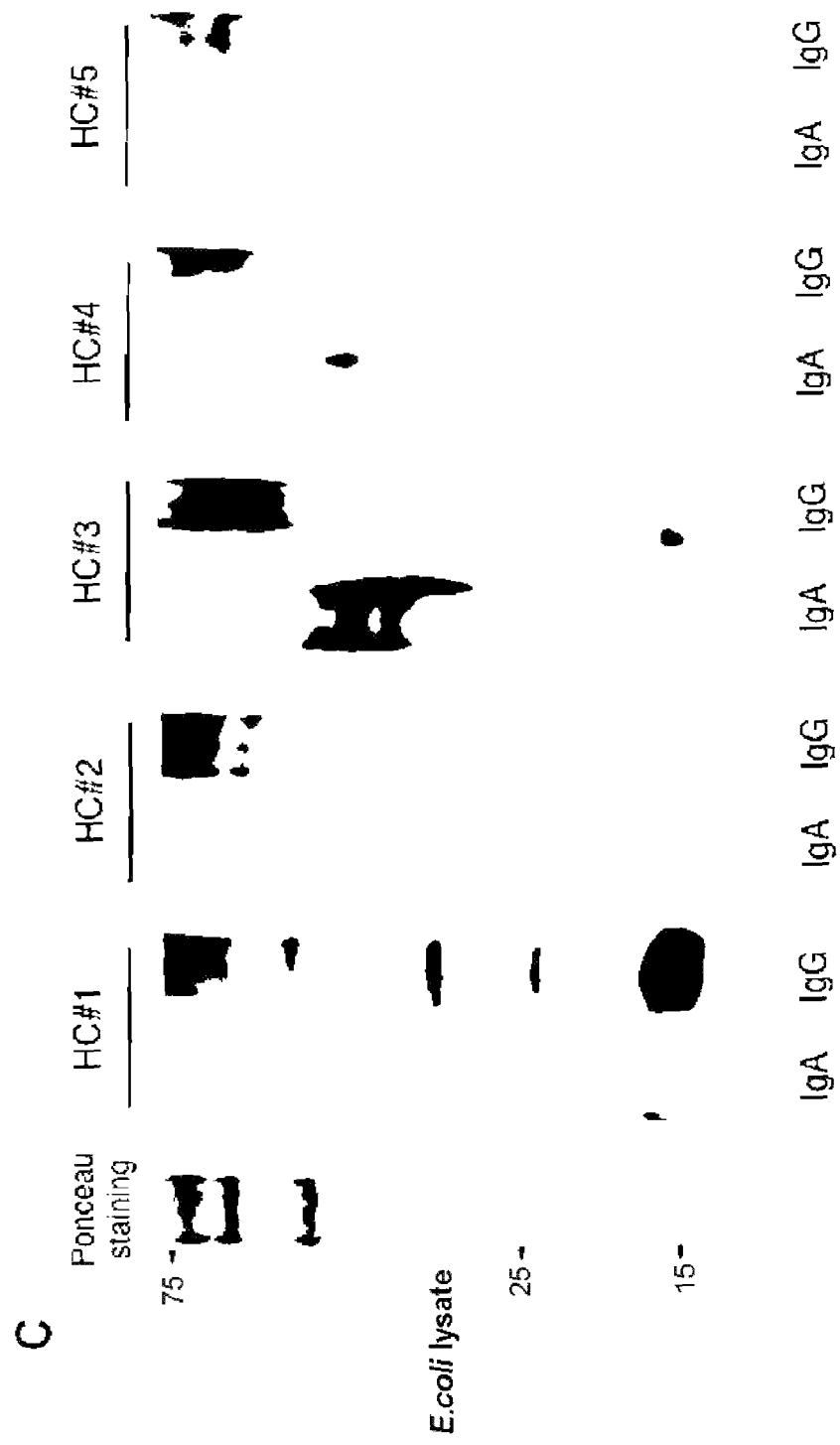

It was previously suggested that murine IgG would target a restricted number of bacterial proteins and favored highly conserved outer membrane proteins[8]. Reactivity of human serum IgG against bacterial lysates from a Gram-negative strains was evaluated by immunoblotting. We observed that IgG labeled several *E. coli* bands (FIG. 2C), suggesting that multiple bacterial products are involved in the induction of systemic antibodies. Interestingly, this analysis reveals a great deal of inter-individual variability, as it is not always the same bacterial products that react with the tested serums. We then compared the overlap between bacterial products labeled by IgG and IgA and found distinct binding profiles (FIG. 2C). Finally, in the 5 individuals tested, although some bacterial products (notably a 15 Kd antigen) are frequently targeted in most subjects and without isotype restriction, it clearly appears that IgA and IgG never share exactly the same binding pattern at a molecular level.

Taken together, these results demonstrate although IgG converges with IgA to bind the surface of commensals, it appears that IgA and IgG do not systematically target the same bacterial antigens, even at the individual level.

Figures 3A, 3B:
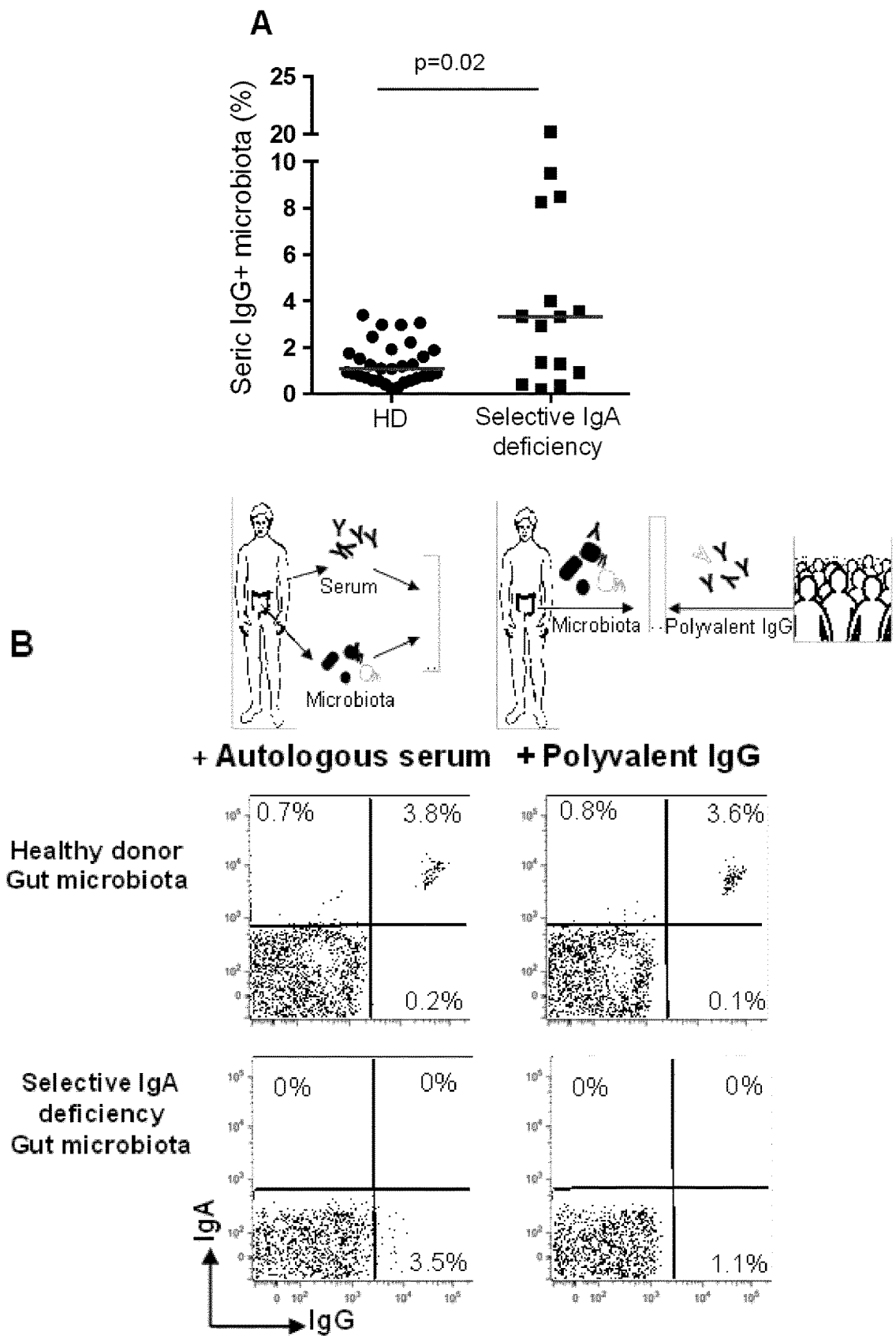
Figures 7A, 7B:
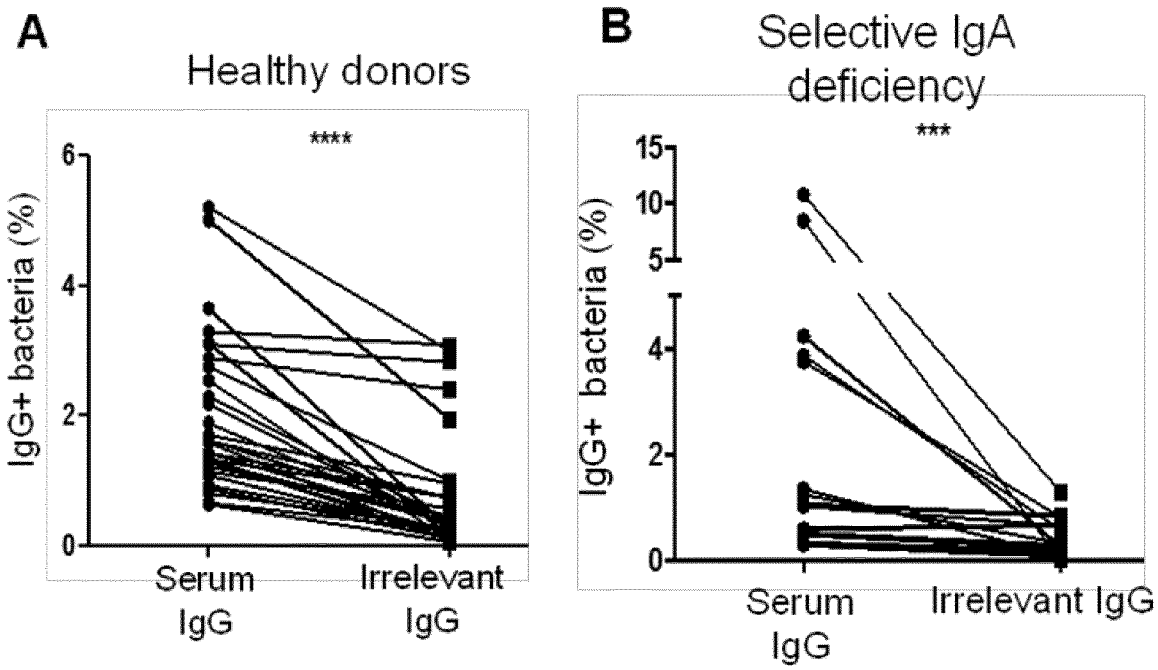

3/ Private Anti-Microbiota IgG Specificities are Induced in IgA-Deficient Patients The existence of seric IgG able to bind IgA-coated bacteria could equally suggest that some gut bacteria (or bacterial antigens) might cross the intestinal barrier: (i) in spite of IgA, or (ii) because of IgA. In order to explore these two putatively opposing roles for IgA, we studied the systemic anti-commensal IgG response in SIgAd. These patients had undetectable seric and digestive IgA levels while seric IgG were in the normal range[15]. Anti-microbiota IgG levels were significantly higher in SIgAd compared to controls (median [min–max]%; 3.3[0.2–20.2]% versus 1.1%[0.2–3.2]%; FIG. 3A). Using irrelevant human IgG, we confirmed that, like in healthy donors, IgG interact with fecal bacteria in a Fab-dependent manner (FIG. 7B). These data support an enhanced triggering of systemic IgG immunity against fecal microbiota when lacking secretory IgA, as shown in the murine model of polymeric immunoglobulin receptor deficiency[6].

Figures 3C, 3D:
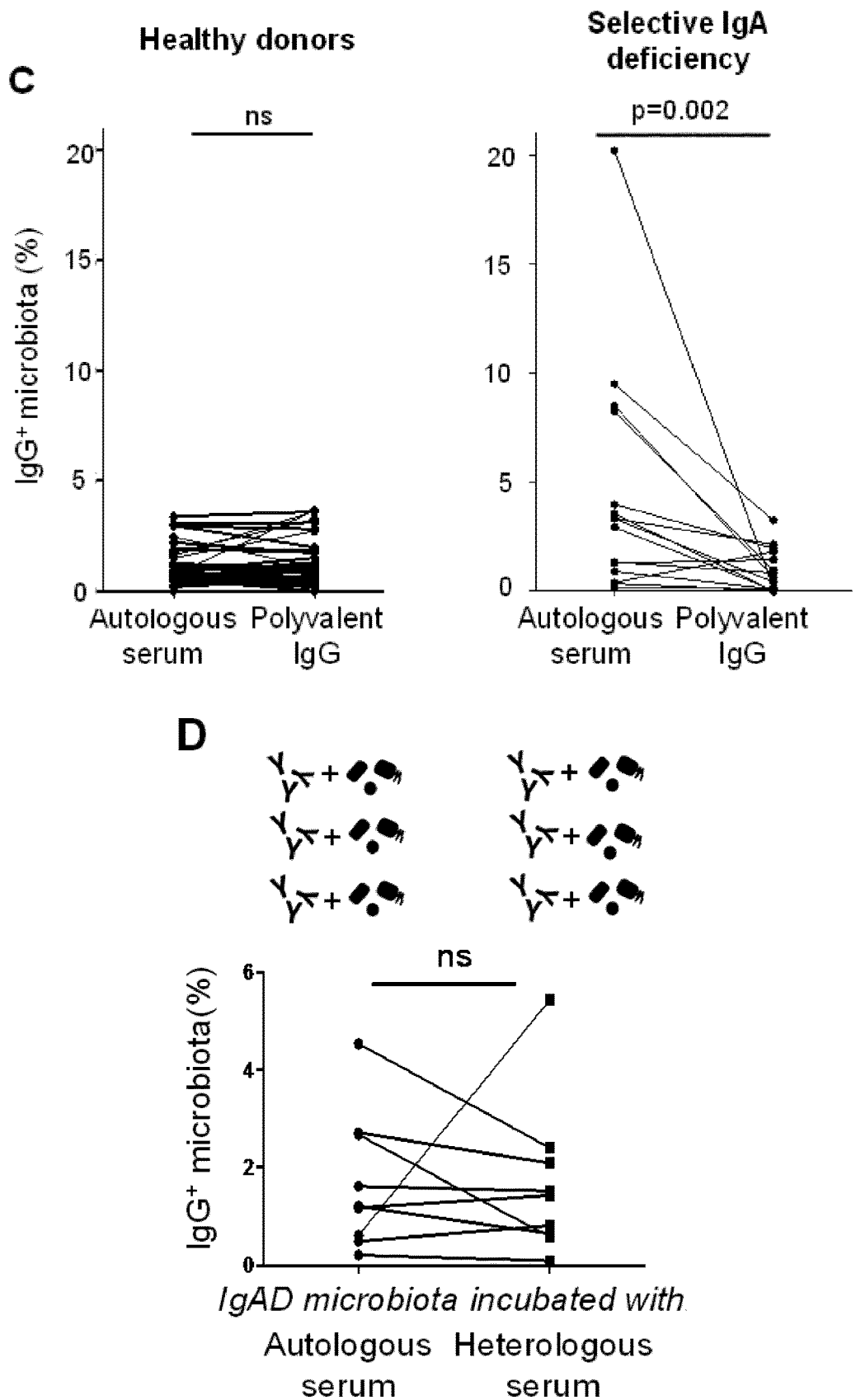
Figure 7C:
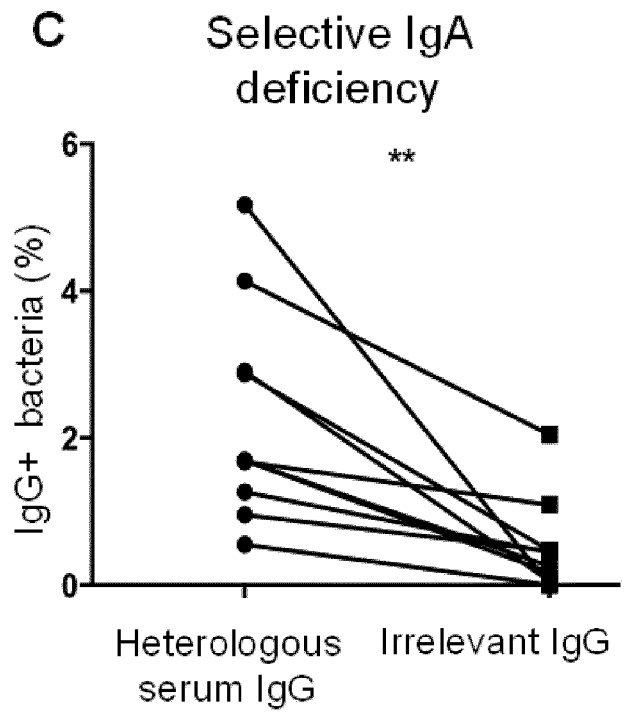

Considering this high level of anti-microbiota IgG in SIgAd, and the similarity of SIgAd and healthy microbiota composition[15], we investigated how anti-microbiota IgG repertoires from healthy donors and IgA deficient patients were overlapping. Using polyclonal IgG from pooled serum of healthy donors, we assessed IgG-bound microbiota using either healthy or SIgAd purified microbiota. We showed that pooled polyclonal IgG and autologous healthy sera recognized a similar percentage of fecal bacteria (median [min–max]%; 1[0–3.7] % vs 1.1[0.2–3.2]%, respectively, FIG. 3B-C). In contrast, pooled polyclonal IgG bound a smaller bacterial fraction of IgA deficient-microbiota compared to autologous patient serum (median [min–max]%; 0.4[0–3.6] % vs 3.3[0.2–20.2] %, FIG. 3B-C). In order to test whether similar specificities are induced in all or most IgA deficient individuals, we compared their IgG reactivity to autologous or heterologous gut microbiota. In this experiment (FIG. 3D), each IgA-deficient microbiota was incubated either with autologous serum (i.e.: autologous condition), or with serum from an unrelated IgA deficient individual (i.e.: heterologous condition). As shown in FIG. 3D, no significant difference was seen between autologous or heterologous conditions (median autologous IgG+ microbiota 1.2% versus median heterologous IgG+ microbiota 1.4%). Of note, heterologous seric IgG also predominantly interact with fecal microbiota in a Fab-dependent manner (FIG. 7C).

This set of data suggests that peculiar anti-microbiota IgG specificities are induced in IgA-deficient patients, but not in healthy individuals.

4/ IgG Specifically Recognize a Broad Spectrum of Bacteria

To more deeply decipher anti-commensal IgG specificities in both healthy donors and IgA deficient patients, we next performed a stringent flow-sorting to isolate IgG-bound bacteria and identified their taxonomy by 16S rRNA sequencing (FIG. 4A). We observed extensive inter-individual variability at genus level irrespective of immunological status (healthy donors vs IgA deficient patients). Microbial diversity calculated by Shannon index varied between donors, but on average bacterial diversity of IgG$^+$ and IgG$^-$ bacteria was not significantly different (FIG. 4B). We postulated that IgG might preferentially interact with dominant taxa, and therefore compared relative abundance of IgG-bound and IgG-unbound genera. Both fractions exhibited equal distributions of rare and abundant genera (FIG. 4C), thus IgG target commensals irrespectively of their frequency. Interestingly, we found that individual IgG$^+$ and IgG$^-$ fecal bacterial profiles were remarkably different, supporting a strong IgG bias against peculiar taxa that cannot be explained by an expansion of the latter. Besides, anti-commensals IgG were not restricted to pathobionts, but also targeted symbiotic genera such as *Faecalibacterium*, whose the most common species (i.e.: *F. prausnitzii*) has been assigned anti-inflammatory properties in both healthy donors and IgA deficient patients[16]. From this part we conclude that anti-commensal IgG recognize a diverse array of both pathobionts and commensal bacteria. Importantly, each individual harbored a private IgG antimicrobial signature.

5/ High Anti-Microbiota IgG Levels Correlate with Reduced Systemic Inflammation

Figures 5A, 5B, 5C, 5D:
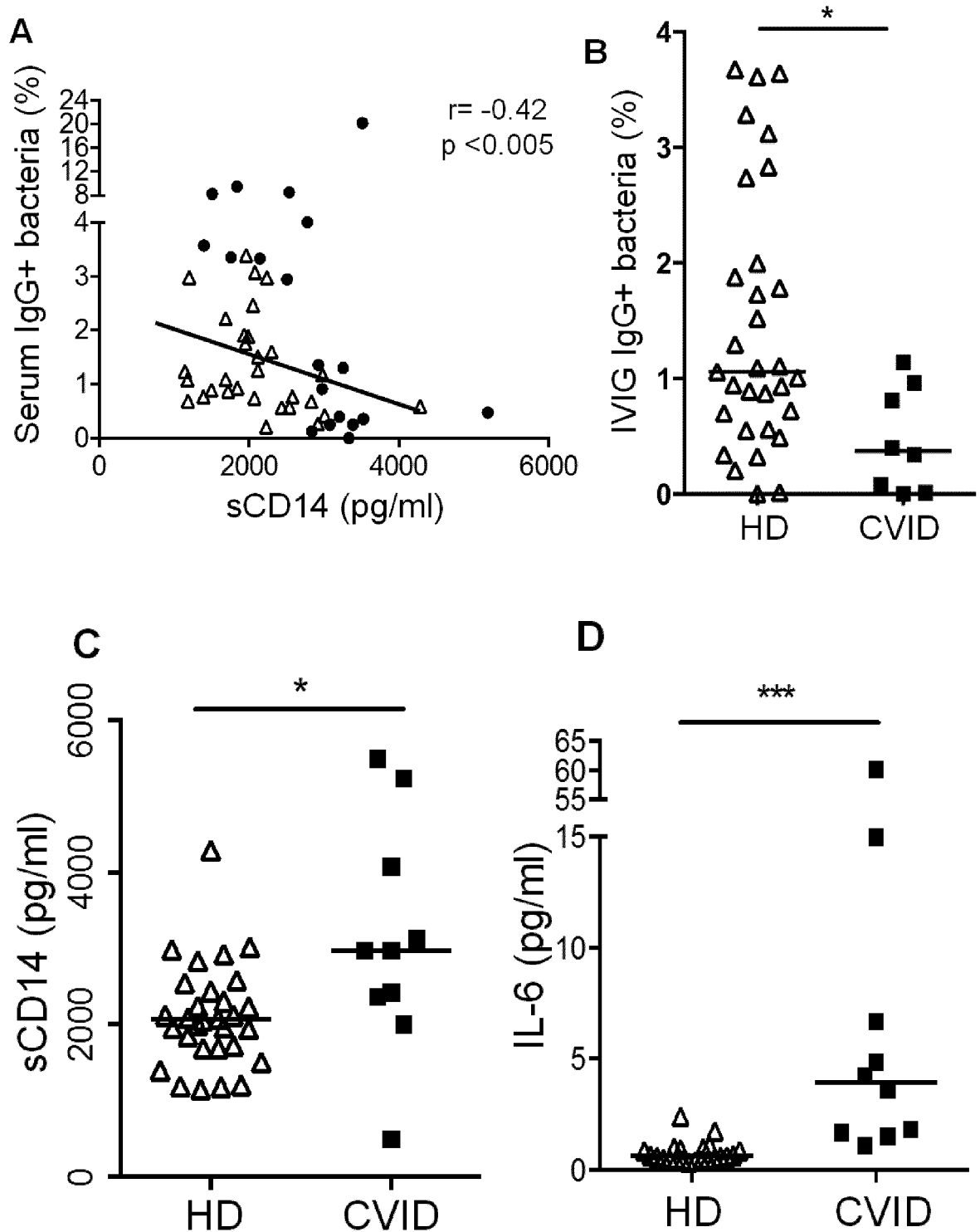
Figure 5E:
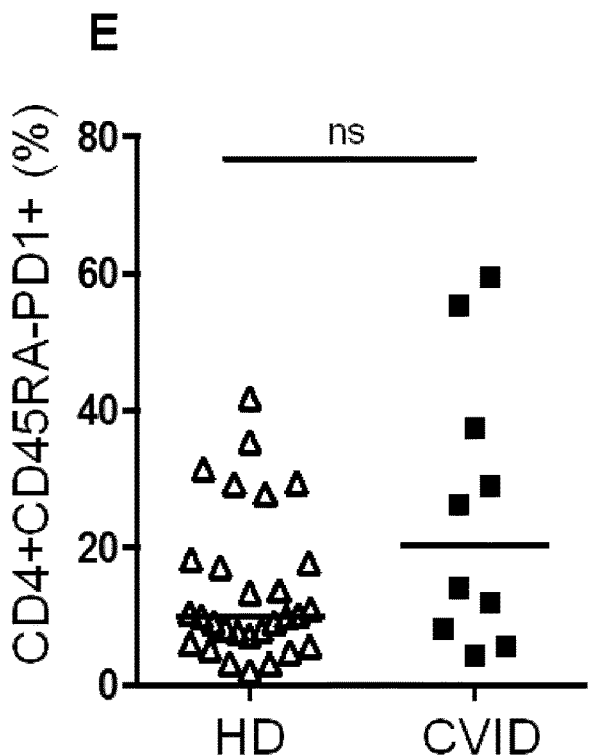

Microbiota-specific serum IgG responses contribute to symbiotic bacteria clearance in periphery and maintain mutualism in mice[2]. We thus hypothesized that anti-commensals IgG might influence the balance of systemic inflammatory versus regulatory responses in humans. Hence, we measured plasma levels of sCD14 (a marker of monocyte activation,[17]) and observed that seric IgG-coated bacteria inversely correlated with soluble CD14 (r=−0.42, p<0.005; FIG. 5A) in both healthy donors and SIgAd patients. These results are in line with the finding that IgG replacement therapy reduced endotoxemia[18]. To further explore the potential link between anti-microbiota IgG and systemic inflammation, we explored CVID patients (characterized by both IgG and IgA defects). These patients benefit from IVIG treatment. Yet, we show that IVIG do not efficiently bind CVID microbiota. As shown in FIG. 5B, IVIG bound a reduced fraction of CVID microbiota compared to control microbiota (median [min–max]%; 0.37[0.00–1.14]% vs 1.06[0.00–3.7]%). We then determined plasma levels of sCD14 and IL-6 (an inflammatory cytokine reflecting T-cell activation) and evaluated the expression of PD-1 (a T-cell co-inhibitory molecule induced after activation) on CD4+ T cells. IL-6 as well as sCD14 levels were consistently higher in CVID patients than in healthy donors (IL–6, median [min–max]%, 1.8(0.7–60.1) pg/ml versus 0.6(0.33–2.4) pg/ml; sCD14, median [min–max]%; 2063 (590–5493) pg/ml versus median 2696(1147–4283) pg/ml; FIG. 5C-D). Moreover, CD45RA-PD1+CD4+ T cells tended to increase in CVID patients, as compared with healthy donors (median [min–max]%; 20.3(4.26–59.6)% versus 10(2.09–41.9)%, FIG. 5E).

Altogether, in both controls and IgA-deficient patients, systemic anti-microbiota IgG responses correlate with reduced inflammation.

Discussion

Anti-commensal IgG have been described in patients with inflammatory diseases[5,19,20]. Here, we characterize for the first time a broad anti-commensal IgG response under homeostatic conditions in humans. Previous work demonstrated that symbiotic Gram-negative bacteria disseminate spontaneously and drive systemic IgG responses[8]. We show here that a diverse array of commensal bacteria, including Gram-positive and Gram-negative species, can induce systemic IgG. We show that a pathobiont like *E. coli* induce less systemic IgG responses than a presumably beneficial symbiont like *B. adolescentis* (FIG. 2B). Therefore the systemic IgG response in healthy humans does not appear preferentially driven by pathobionts, but also by commensals. In mice it has been shown that commensal microbes induce serum IgA responses that protect against sepsis[21], illustrating the consequence of systemic anti-microbial IgA binding to both pathogenic strains and commensals. We postulate that systemic anti-microbiota IgG, also mainly induced by commensals, could have the same protective role.

Strikingly, systemic IgG and secretory IgA converge towards the same autologous microbiota subset. Yet, it seems unlikely that secretory IgA enhances systemic IgG responses, since IgA deficiency is associated with high proportions of IgG+ microbiota, as detected using bacterial flow cytometry on SIgAd microbiota labeled with autologous serum. In addition, induction of anti-commensal IgG has been shown to be microbiota-dependent, but IgA-independent in mice[2,6]. Systemic IgG could reflect asymptomatic gut microbiota translocation episodes in healthy individuals. Repeated bacterial translocations might occur more frequently in the absence of secretory IgA, accounting for elevated anti-microbiota IgG levels in these patients.

IgA do not activate complement via the classical pathway[22]. Interestingly, the anti-*Bifidobacterium adolescentis* IgG response is primarily restricted to the IgG2 isotype (Figure S3), which less efficiently triggers the classical route of complement than IgG1 and IgG3[23]. Furthermore, IgG2 poorly interact with type I FcγRs, while IgG1 and IgG3 demonstrate affinity for most FcγRs[24]. These distinct binding patterns have functional consequences. IgG1 antibodies mediate phagocytosis and induce potent pro-inflammatory pathways while IgG2 are rather involved in dendritic cell or B cell activation[25,26]. Besides its specific Fc domain interaction, IgG2 is usually, but not exclusively, associated with anti-carbohydrate responses[27]. IgA was also recently shown to bind multiple microbial glycans[28]. Thus, IgA and IgG2 could be viewed as playing similar roles, but in different compartments. Much effort has been recently expended to develop bacterial glycan or protein microarray. Glycomics could represent a new option in order to better decipher anti-microbiota antibody targets[27,29].

Importantly, we show that IgA and IgG do not systematically target the same bacterial antigens at an individual level (FIG. 2C). Therefore IgG and IgA epitopes are not strictly overlapping. This result could further illustrate antibacterial IgA/IgG synergy, and explain the absence of isotype competition allowing the observed IgA/IgG co-staining of bacteria (FIG. 1).

Recent studies suggested that murine secretory IgA are polyreactive and bind a broad but defined subset of microbiota[30,31]. Similarly, up to 25% of intestinal IgG+ plasmablasts could produce polyreactive antibodies[9]. We therefore hypothesized that the cross-reactive potential of anti-commensal IgG may act as a first line of defense against potentially harmful bacteria. In line with this idea, it can be noted that homeostatic anti-commensal IgG confer protection against pathogens such as Salmonella[8]. Conversely, IgG directed against Klebsiella pneumoniae, an opportunistic pathogen, cross-react with commensal microbes[32]. Clonally related memory B cells expressing cross-specific anti-K. pneumoniae antibodies were found in both lamina propria and peripheral blood in humans suggesting that generation of anti-commensal antibodies might be triggered in the mucosal compartment. At the same time, anti-commensal memory B cells might recirculate in periphery[32]. Altogether, it appears possible that bacteria-specific IgG would arise from the gut, as all bacteria-specific IgG isotypes we characterized in human sera are also present in the gut (data not shown), and also because a large proportion of gut IgG+ B cells are expected to be commensal-specific[9]. However, it remains presently unknown whether serum IgG responses mainly originate from the gut and/or are induced the periphery following bacterial translocation.

We report that each individual harbors a private set of anti-commensal IgG in both healthy donors and IgA deficient patients. Since our analysis was limited to 3 IgA deficient patients, further study might precisely reveal how SIgAd anti-commensal IgG bind a distinct set of commensals. While IVIG preparations contain an extended set of anti-commensal IgG, we observe that IVIG less efficiently bind CVID microbiota. These observations are consistent with reported alterations of gut microbiota in CVID patients[33]. Microbiota perturbations are also associated with selective IgA deficiency. The latter perturbations are less pronounced than in CVID, since the presence of IgM appears to preserve SIgAd microbiota diversity[15]. Nevertheless, IgA deficiency condition is also associated in severe cases with bacterial translocation, colitis and dysbiosis. These complications are not accessible to substitutive Ig replacement therapy[34]. Indeed, IVIG do not appear to contain high-enough concentrations as well as appropriate specificities of anti-commensal IgG. As shown in FIG. 3, healthy control serum usually less efficiently binds IgA deficient microbiota than autologous serum. Similarly, IVIG poorly targets CVID gut microbiota (FIG. 5B). In addition, local mucosal antibody responses might be important in regulating microbiota composition in a way that cannot be substituted by IVIG. These findings expand our understanding of how IVIG fail to treat gastro-intestinal symptoms in CVID and IgA deficient patients. Dysbiosis and gastro-intestinal complications might not accessible to substitutive Ig replacement therapy, since, as we show, healthy IgG repertoire does not contain adequate "dysbiotic-specific" antibodies.

It was recently shown in mice that maternally-derived anti-commensal IgG dampen aberrant mucosal immune responses and strengthen epithelial barrier[7,35]. The contribution of systemic anti-commensal IgG to the regulation of microbiota/immune homeostasis was not explored in the latter studies. Here, we show that anti-commensal IgG are negatively associated with sCD14, suggesting they might quell inflammation. In support of this, we measured higher levels of sCD14 and IL-6 in plasma of patients lacking both IgA and IgG compared to controls (FIG. 5).

Altogether, these data suggest that systemic IgG and intestinal IgA cooperate in different body compartments to limit systemic pro-inflammatory pathways. While selective IgA deficient patients harbour elevated seric anti commensal IgG levels, CVID patients can not mount an appropriate IgG response. These findings suggest that: in selective IgA deficiency, microbiota confinement is obtained at the price of a strong inflammatory response, and in CVID, confinement is lost and Ig replacement therapy do not substitute for a specific autologous IgG response. We therefore propose that IgA supplementation might have beneficial effects on gut dysbiosis and systemic inflammatory disorders associated with antibody deficiencies. IgA might be orally delivered through a carrier system allowing colon delivery. Polymers such as gellan gum or pectin, are degraded specifically by the colonic microbiota and could thus release polymer-bound IgA locally[36].

In summary, we report for the first time a systemic anti-commensal IgG response that is restricted to intestinal IgA-coated bacteria in humans. We demonstrate that in the absence of IgA, anti-commensal IgG responses are amplified and associated with reduced systemic inflammation. Finally, the present study provides new therapeutic perspectives based on IgA supplementation in patients with CVID or SIgAd, while SIgAd-derived IgG supplementation might be considered in CVID.

EXAMPLE 2

Material & Methods
Human Specimens

Surgical samples from histologically normal ascending colon were obtained from colon cancer patients undergoing hemi-colectomy (Department of Surgery, Pitié-Salpêtrière hospital, Paris). Patients with a history of intestinal inflammation were excluded from the study. Ileostomy fluids were collected from intensive care unit patients (Table S2). Fresh stool and blood samples were collected from 20 healthy volunteers (Fadlallah et al., 2018). Fresh stools from three IgA deficient patients with undetectable serum IgA levels (<0.07 mg/ml) were obtained from the Department of Clinical Immunology at St Louis hospital, Paris (Fadlallah et al., 2018). Antibiotic therapy or diarrhea in the last three months were exclusion criteria in all instances. Maternal milk was obtained from three healthy donors. Stool samples, maternal milk and plasma were immediately frozen after collection and stored at 527-80° C. until use. All individuals signed a written consent and the protocol was approved by the local ethical committee of the Pitié-Salpêtrière hospital.

Stool Processing and Microbiota Purification.

Fresh feces were aliquoted in a CO2 rich—O2 low atmosphere and stored at −80° C. Then microbiota were isolated by gradient purification under anaerobic conditions, as previsouly described (Juste et al., 2014). In brief, a density gradient of Nycodenz solution was prepared. Then, thawed stool was diluted in 1×-PBS (Eurobio), 60% Nycodenz, 0.03% sodium deoxycholate (NaDC) and loaded on the gradient. After ultracentrifugation (45 min, 14567×g, 4° C.; Beckman Coulter ultracentrifuge), fecal bacteria were extracted and washed three times in 1×-PBS, 0.03% NaDC and centrifuged. The final bacterial pellet was diluted in 1×PBS-10% glycerol, immediately frozen in liquid nitrogen and stored at −80° C.

Bacterial Strains and Culture Conditions

*Staphylococcus epidermidis*, *Staphylococcus aureus* and *Staphylococcus haemolyticus* were isolated from human stool samples and identified by MALDI-TOF mass spectrometry (Microbiology department, Pitié Salpêtrière hospital, Paris). *Bifidobacterium longum* (E194v variantA) and *Bacteroides vulgatus* (NCTC11154) were collected and characterized at the Institut National de Recherche Agronomique (INRA; Jouy en Josas, France). Bacterial strains were cultured on sheep red blood agar plates at 37° C. under aerobic (*Staphylococcus* sp, for 24 h) or anaerobic (*Bacteroides vulgatus* for 24 h and *Bifidobacterium longum* for 48 h) conditions. Individual colonies were picked, suspended in 1×-PBS-10× glycerol (109 CFU/ml) and frozen at −80° C. Quantification of colony forming units (CFU) was performed by adding counting beads (Beckman Coulter) to bacterial suspensions on a flow cytometer (FACS Canto IITM551, BD).

Production of Human mAbs

For IgA production from long-term clonal B cell cultures, B cells were isolated from colonic lamina propria dissected into 2 mm pieces and digested by the addition of collagenase in 1×PBS (50 mg/ml, Roche), then incubated at 37° C. for 40 minutes (min). Lymphocytes were purified by centrifugation over Ficoll 400 (Eurobio) and stained with the following antibodies: anti-CD45 APC-H7, anti-CD19 BV421, anti-IgD FITC, anti-IgM BV605, anti-CD27 PE-Cy7 (all purchased from BD Biosciences) and anti-IgA PE (Jackson Immunoresearch). Dead cells were excluded with LIVE/DEAD™ 560 Fixable Aqua Dead Cell Stain Kit (Invitrogen). CD45+CD19+CD27+IgD-561 IgM-IgA+ B cells were sorted on a FACS Aria II™ cytometer (BD). B cells were cultured for 4 days, in the presence of irradiated (50 Gy) mouse fibroblasts expressing CD40L, at a concentration of 104 cells per well (Arpin et al., 1995) and recombinant IL-21 (50 ng/ml, a kind gift of Dr Arjen Bakker, AIMM Therapeutics, Amsterdam, The Netherlands) in IMDM (LifeTechnologies), containing 10% FCS (Biowest) in a 96-well flat bottom plate. Retroviral transduction was performed with a Bcl-6 and BclxL-expressing retroviral construct (AIMM Therapeutics), using the experimental conditions as described (Kwakkenbos et al., 2010). Briefly, activated B cells were incubated with retroviral supernatant and polybrene (Sigma, final concentration 4 μg/ml) in a 96-well flat bottom plate, coated with the recombinant human fibronectin fragment CH-296 (Takara) for 8 h at 37° C. After washing, the cells were cultured for 4 days in the presence of irradiated CD40L expressing mouse fibroblasts and recombinant IL-21 (50 ng/ml) in IMDM-10% FCS in 96-well flat bottom plates. Transduction efficiency based on GFP expression was monitored at day 4. B cells clones were then obtained by limiting dilution cultures and IgA were concentrated from culture supernatants with Amicon® centrifugal filters (Millipore). Human mAbs obtained through single-cell PCR processing of isolated IgA-producing colonic lamina propria B cells expressed variable IgA domains fused to human IgG1 constant domains in HEK293T cells, as previously described (Benckert et al., 2011).

Sorting of IgA-Bound Microbiota

Gut microbiota obtained from an IgA deficient patient was incubated with purified mAbs (final concentration 1 μg/ml) in a 96-well V-bottom plate (107 bacteria/well, 10 wells/mAb) for 30 min at 4° C. After washing with 1×-PBS (10 min, 4000×g, 4° C.), cells were stained with goat anti-human IgA-FITC (1/200) or isotype control antibody (Jackson Immunoresearch Laboratories). For sorting of in vivo IgA1 or IgA2-bound commensal bacteria, purified microbiota from 5 healthy donors were thawed, washed and directly stained with mouse anti-human IgA1-FITC or mouse anti-human IgA2 Alexa Fluor 647 (Southern Biotech) in a 96-well V-bottom plate (107 bacteria/well, 5 wells/subclass) for 20 min at 4° C. After washing, sorting was performed using a S3 cell sorter (Bio-Rad Laboratories, California, USA). Sorted bacteria (9.105) were collected in 1×-PBS at 4° C., centrifuged (8000×g, 10 min, 4° C.) and stored at −80° C. until DNA extraction. Purity for both fractions was systematically verified after sorting. To check the absence of contaminants in flow cytometer fluid lines, sheath fluid was regularly incubated in Brain-Heart Infusion Broth (BioMérieux) at 37° C. for 7 days.

16S rRNA Gene Sequencing and Analysis

DNA was extracted using Trizol (Ambion), according to the manufacturer's instructions. Amplicons of V3-V4 regions of 16S rRNA genes were generated in a PCR mix containing, 5 μl of extracted DNA, 500 units of MolTaq 16S (Molzym), 10 mM dNTP (Invitrogen), 10 pmol/μl V3-external and V4-external primers (Table S3) in MolTaq buffer (Molzym) diluted in DNA-free water (Molzym) for a final volume of 50 μl. 2 μl of first round PCR reaction (95° C. 10', 95° C. 1'—54° C. 1'—72° C. 1' 10 times, final extension 72° C. 10') were used as template in a second round PCR (95° C. 10', 95° C. 1'—66° C. 1'—72° C. 1' 10 times, final extension 72° C. 10') with V3-V4 barcoded primers (Table S3). PCR products were purified using paramagnetic beads (Agencourt® Ampure® XP, Beckman Coulter) and sequenced on a MiSeq instrument (Illumina) in a multiplexed sequencing run (paired-end 250 nucleotides reads) at iGenSeq ICM facility (Institut du Cerveau et de la Moelle Epinière, Paris, France). De-multiplexed reads were processed using MG-RAST analysis pipeline. Sequencing artefacts, host DNA contamination and sequences less than 200 bp in length were removed. Insufficient quality reads were discarded (<5% of total reads). Sequences were then clustered into operational taxonomic units (OTUs) with a 97% homology using Greengenes database. OTUs containing only a single sequence were discarded. Previously published contaminant sequences (Salter et al., 2014) were removed if present in only one sorted fraction and absent from paired fractions. OTUs detected at >0.1% relative abundance in at least 2 samples were finally conserved. This process reduced the total OTU count from 313 down to 178. OTU table was rarefied to the minimum sample's depth (5000 reads). Shannon index was calculated according to the following equation: Shannon index=−Σ $p_i$ ln($p_i$) where $p_i$ is the relative abundance of the ith OTU in the dataset. In calculating the enrichment index EI (formula shown in Figure), we scored a pseudo-relative abundance equal to 0.0001, which was the lower limit of detection, if a taxon was not detected in a given fraction. Specificity of IgA1+IgA2+ targeting was calculated using the following formula:

$$\frac{\text{Number of samples in which } OTU \text{ had a positive } IgA1IgA2 \text{ Enrichment Index}}{\text{Number of samples}}.$$

Specificity of IgA2+ targeting was calculated with the formula:

$$\frac{\text{Number of samples in which } OTU \text{ had a negative } IgA1/IgA2 \text{ Enrichment Index}}{\text{Number of samples}}.$$

Statistical Analysis

Statistical analysis was performed using Graphpad Prism® v6. Non parametric tests were used whenever necessary: Wilcoxon paired rank test was used when comparing paired groups, Mann-Whitney test when comparing two independent groups, Kruskall Wallis for multiple comparisons. Significant p values (p<0.05) are indicated on plots (* p<0.05; p<0.01; *<0.001). Hierarchical clustering algorithms were run with Partek® software or "R" (The R Foundation for Statistical Computing, version 3.4.3).

Result

Intestinal IgA Clones Target Highly Diverse Commensal Bacteria

Figure 8A:
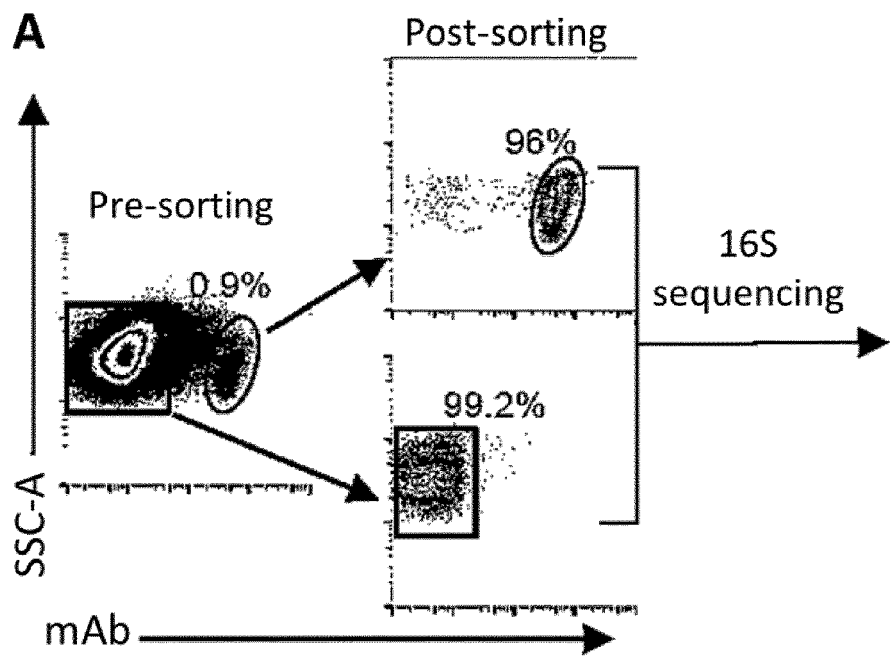
Figure 8B:
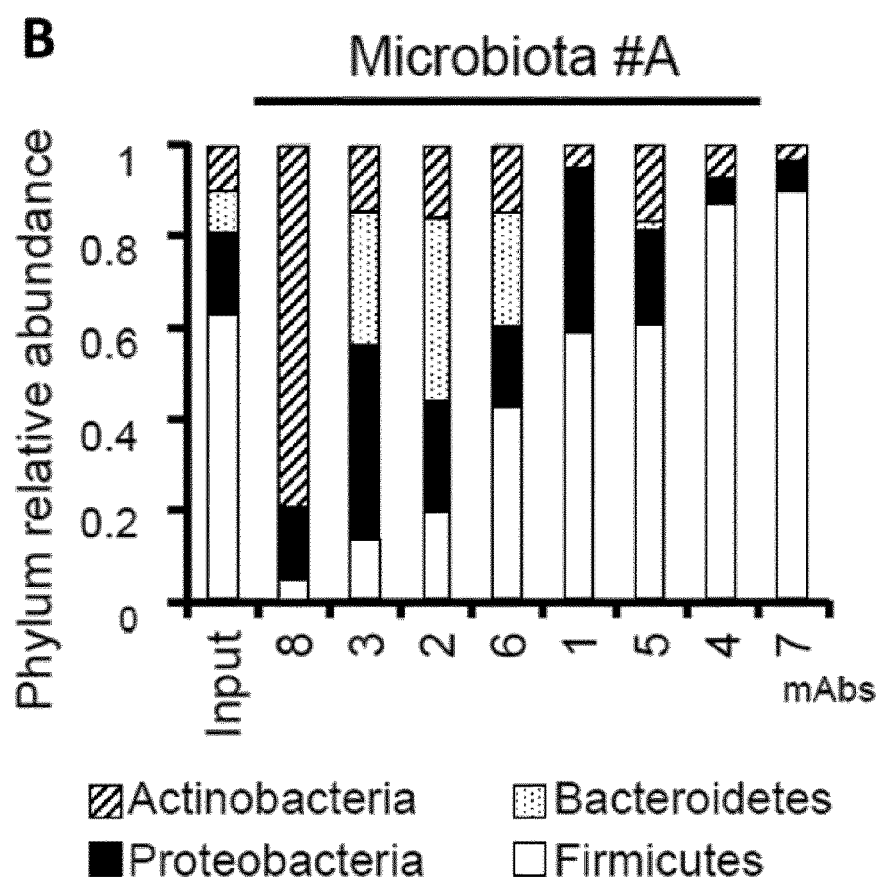
Figure 8C:
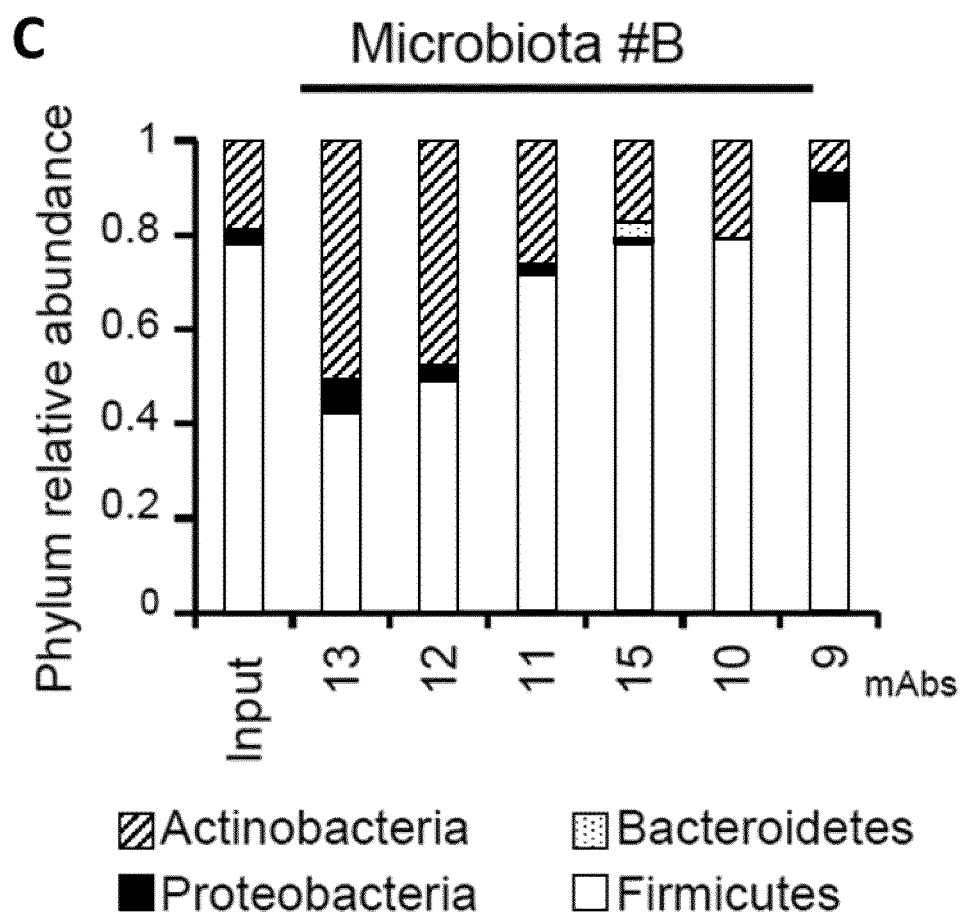

To characterize commensal bacteria from microbiota #A/#B bound by IgA, we separated mAb-bound (mAb$^+$) from mAb-free (mAb$^-$) microbiota, using stringent fluorescent-activated cell sorting. We then identified bacteria in sorted fractions by 16s rRNA gene sequencing (FIG. 8A). The mAbs recognized the four major phyla, namely Actinobacteria, Bacteroidetes, Firmicutes and Proteobacteria, with unique binding profiles for each (FIG. 8B-C). Results from a genus-level analysis corroborated these distinct binding patterns and highlighted the cross-reactivity of the mAbs showing that they targeted numerous genera (such as *Corynebacterium, Flavobacterium, Blautia, Faecalibacterium, Ruminococcus, Paracoccus, Clostridium, Roseburia, Staphylococcus, Acinetobacter, Pseudomonas, Bradyrhizobium, Eubacterium, Hespellia, Nocardia, Bifidobacterium, Desulfohalobium* or *Butyrivibrio* for example) irrespective of their microbial phylogeny (data not shown). These data therefore indicate that a single mAb might recognize a wide panel of bacterial epitopes. Because mAb reactivity extended to unrelated genera, we tested whether genus abundance might influence mAb binding patterns. We found that genera in mAb$^+$ and mAb$^-$ fractions did not differ in terms of relative abundance (median of genera relative abundance 0.00123[0.000284–0.0056] in the mAb$^+$ fraction vs 0.0008[0.00026–0.00159] in the mAb$^-$ fraction, p=0.27; data not shown).

Moreover, 12 out of the 50 most abundant genera were never targeted by mAbs (*Eggerthella, Bacteroides, Parabacteroides, Anaerostipes, Kingella, Neisseria* and *Pelomonas* in microbiota A; *Tissierella, Peptostreptococcus, Paenibacillus*, Microbacteriuma and *Helcococcus* in microbiota B; data not shown), thereby implying that IgA antibodies react with various commensal microbes regardless of their bacterial richness. Interestingly, mAb binding profiles recapitulated common IgA-targeted microbes in humans including *Ruminococcus, Roseburia, Clostridium* and *Blautia* (data not shown) (D'Auria et al., 2013; Palm et al., 2014; Magri et al., 2017).

Discussion

In the present study, we show that human intestinal IgA bind at a clonal level a wide, but distinct, subset of microbiota, including commensals from the four most frequent phyla. This reactivity extended to numerous genera, regardless of their phylogenetic distance or their relative abundance. One of sixteen mAbs that were generated from intestinal B cells displayed both microbiota-reactivity and self-reactivity, resembling the 15% self-reactive plasmablasts described in the lamina propria (Benckert et al., 2011). While the molecular basis for this broad antibody reactivity spectrum remains unclear, it has been proposed that IgA binding may involve different affinity interactions with variant antigens of commensal species (Pabst, 2012). Although we could not reliably measure the affinity of antibodies to bacterial cells, we observed (i) a wide scale of staining intensity and (ii) variations across enrichment indexes in mAb+ fractions, that strongly support low to high-affinity interactions with commensals. Of note, IgA cross-reactivity does not imply random interactions. On the contrary, IgA interactions appeared rather selective as, for instance, *Staphylococcus epidermidis* evaded those IgA antibodies that target both *Staphylococcus aureus* and *Staphylococcus haemolyticus*.

Our observations raise the issue of the respective functional roles of IgA1 and IgA2 and the respective impact they may have on microbiota diversification along the gastro intestinal tract. We show that both IgA1 and IgA2 induce the production of pro-inflammatory cytokines, while the regulatory cytokine IL-10 was preferentially induced by IgA1-coated bacteria in vitro (data not shown). While IgA1+ IgA2+ bacteria are predominant in the ileum, we observe that IgA2 accounts for most colonic commensal binding. The colonic IgA2-only coated microbiota is dominated by three genera belonging to the phylum Bacteroidetes (*Bacteroides, Prevotella* and *Flavobacterium*). One tentative explanation for this finding might be the longer transit time and the availability of complex polysaccharides in the colon that facilitate the growth of anaerobes such as Bacteroidaceae and Prevotellaceae (Donaldson et al., 2016). In contrast, bacteria coated by both IgA1 and IgA2 such as *Clostridium* sp., and additional genera from Actinobacteria (e.g. *Bifidobacterium*) and Proteobacteria phyla (e.g. *Serratia*), are, as expected, usually described to reside in the small intestine (Sekirov et al., 2010; Donaldson et al., 2016). These observations suggest that both IgA1 and IgA2 responses are elicited in the small intestine, while the colon would be the dedicated site for IgA2-only responses. Bacteria coated by both subclasses in the colon may represent transient bacteria from the ileum. Indeed, while in IgA1+ and IgA2+ B cells are found in similar proportions in the small intestine, IgA2+ B cells are preponderant in the colon (He et al., 2007). One could therefore speculate that IgA2 is essential for diversification of the colonic microbiota, whereas IgA1 is preferentially induced in the ileum. Homeostatic secretory IgM responses have been described in humans but not in mice.

Secretory IgM target a fraction of mucus-embedded commensals that are also coated by IgA in human colon and ileum (Magri et al., 2017). These observations notwithstanding we could detect fecal IgM-bound bacteria in luminal content of only 5 out of 20 healthy donors, underscoring the presence of an IgM-bound bacterial gradient from the epithelium to the lumen. IgM may help IgA to localize bacteria to be targeted in a favorable habitat in mucus. Indeed, IgM-bound bacteria are also recognized by IgA1 and IgA2. Consistent with this finding, Magri et al. noticed that IgM coat IgA bright bacteria (Magri et al., 2017).

In summary, we show that although IgA induction is antigen-dependent with highly mutated memory clonotypes, IgA microbiota binding patterns are broad, but nevertheless clonotype-specific. Similarly, at the polyclonal level, IgA2 and IgA1 targets are broad and partially overlapping, particularly in the ileum where IgA1+-IgA2+ bacteria are prevalent among IgA-bound microbiota. In all cases, glycan reactivity did not only account for the observed cross-reactivity, but also for selectivity. IgA2 and IgA1 anti-commensal responses are observed as early as three months after birth, suggesting that both isotypes are induced during initial gut colonization by healthy microbiota.

REFERENCES

Throughout this application, various references describe the state of the art to which this invention pertains. The disclosures of these references are hereby incorporated by reference into the present disclosure.
1. Honda K, Littman D R. The microbiota in adaptive immune homeostasis and disease. Nature. 2016; 535:75.
2. Slack E, Hapfelmeier S, Stecher B, Velykoredko Y, Stoel M, Lawson M A E, et al. Innate and adaptive immunity cooperate flexibly to maintain host-microbiota mutualism. Science. 2009; 325:617-20.
3. Donskey C J. The role of the intestinal tract as a reservoir and source for transmission of nosocomial pathogens. Clin Infect Dis Off Publ Infect Dis Soc Am. 2004; 39:219-26.
4. MacFie J. Current status of bacterial translocation as a cause of surgical sepsis. Br Med Bull. 2004; 71:1-11.
5. Beaugerie L, Sokol H. Clinical, serological and genetic predictors of inflammatory bowel disease course. World J Gastroenterol. 2012; 18:3806-13.
6. Johansen F E, Pekna M, Norderhaug I N, Haneberg B, Hietala M A, Krajci P, et al. Absence of epithelial immunoglobulin A transport, with increased mucosal leakiness, in polymeric immunoglobulin receptor/secretory component-deficient mice. J Exp Med. 1999; 190:915-22.
7. Koch M A, Reiner G L, Lugo K A, Kreuk L S M, Stanbery A G, Ansaldo E, et al. Maternal IgG and IgA Antibodies Dampen Mucosal T Helper Cell Responses in Early Life. Cell. 2016; 165:827-41.
8. Zeng M Y, Cisalpino D, Varadarajan S, Hellman J, Warren H S, Cascalho M, et al. Gut Microbiota-Induced Immunoglobulin G Controls Systemic Infection by Symbiotic Bacteria and Pathogens. Immunity. 2016; 44:647-58.
9. Benckert J, Schmolka N, Kreschel C, Zoller M J, Sturm A, Wiedenmann B, et al. The majority of intestinal IgA+ and IgG+ plasmablasts in the human gut are antigen-specific. J Clin Invest. 2011; 121:1946-55.
10. Iversen R, Snir Ø, Stensland M, Kroll J E, Steinsbo Ø, Korponay-Szabo I R, et al. Strong Clonal Relatedness between Serum and Gut IgA despite Different Plasma Cell Origins. Cell Rep. 2017; 20:2357-67.
11. Moor K, Fadlallah J, Toska A, Sterlin D, Balmer M L, Macpherson A J, et al. Analysis of bacterial-surface-specific antibodies in body fluids using bacterial flow cytometry. Nat Protoc. 2016; 11:1531-53.
12. Palm N W, de Zoete M R, Cullen T W, Barry N A, Stefanowski J, Hao L, et al. Immunoglobulin A coating identifies colitogenic bacteria in inflammatory bowel disease. Cell. 2014; 158:1000-10.
13. D'Auria G, Peris-Bondia F, Munkova M, Mira A, Collado M C, Latorre A, et al. Active and secreted IgA-coated bacterial fractions from the human gut reveal an under-represented microbiota core. Sci Rep. 2013; 3:3515.
14. Kau A L, Planer J D, Liu J, Rao S, Yatsunenko T, Trehan I, et al. Functional characterization of IgA-targeted bacterial taxa from undernourished Malawian children that produce diet-dependent enteropathy. Sci Transl Med. 2015; 7:276ra24.
15. Fadlallah J, El Kafsi H, Sterlin D, Juste C, Parizot C, Dorgham K, et al. Microbial ecology perturbation in human IgA deficiency. Sci Transl Med. 2018; 10.
16. Sokol H, Pigneur B, Watterlot L, Lakhdari O, Bermúdez-Humarán L G, Gratadoux J-J, et al. *Faecalibacterium prausnitzii* is an anti-inflammatory commensal bacterium identified by gut microbiota analysis of Crohn disease patients. Proc Natl Acad Sci USA. 2008; 105:16731-6.
17. Bazil V, Strominger J L. Shedding as a mechanism of down-modulation of CD14 on stimulated human monocytes. J Immunol Baltim Md. 1950.1991; 147:1567-74.
18. Perreau M, Vigano S, Bellanger F, Pellaton C, Buss G, Comte D, et al. Exhaustion of bacteria-specific CD4 T cells and microbial translocation in common variable immunodeficiency disorders. J Exp Med. 2014; 211:2033-45.
19. Landers C J, Cohavy O, Misra R, Yang H, Lin Y-C, Braun J, et al. Selected loss of tolerance evidenced by Crohn's disease-associated immune responses to auto- and microbial antigens. Gastroenterology. 2002; 123:689-99.
20. Macpherson A, Khoo U Y, Forgacs I, Philpott-Howard J, Bjarnason I. Mucosal antibodies in inflammatory bowel disease are directed against intestinal bacteria. Gut. 1996; 38:365-75.
21. Wilmore J R, Gaudette B T, Gomez Atria D, Hashemi T, Jones D D, Gardner C A, et al. Commensal Microbes Induce Serum IgA Responses that Protect against Polymicrobial Sepsis. Cell Host Microbe. 2018; 23:302-311.e3.
22. Russell M W, Mansa B. Complement-fixing properties of human IgA antibodies. Alternative pathway complement activation by plastic-bound, but not specific antigen-bound, IgA. Scand J Immunol. 1989; 30:175-83.
23. Bindon C I, Hale G, Brüggemann M, Waldmann H. Human monoclonal IgG isotypes differ in complement activating function at the level of C4 as well as C1q. J Exp Med. 1988; 168:127-42.
24. Bruhns P, Iannascoli B, England P, Mancardi D A, Fernandez N, Jorieux S, et al. Specificity and affinity of human Fcgamma receptors and their polymorphic variants for human IgG subclasses. Blood. 2009; 113:3716-25.
25. Nimmerjahn F, Gordan S, Lux A. FcγR dependent mechanisms of cytotoxic, agonistic, and neutralizing antibody activities. Trends Immunol. 2015; 36:325-36.
26. White A L, Chan HTC, French R R, Willoughby J, Mockridge C I, Roghanian A, et al. Conformation of the human immunoglobulin G2 hinge imparts superagonistic properties to immunostimulatory anticancer antibodies. Cancer Cell. 2015; 27:138-48.
27. Schneider C, Smith D F, Cummings R D, Boligan K F, Hamilton R G, Bochner B S, et al. The human IgG anti-carbohydrate repertoire exhibits a universal architecture and contains specificity for microbial attachment sites. Sci Transl Med. 2015; 7:269ra1.
28. Bunker J J, Erickson S A, Flynn T M, Henry C, Koval J C, Meisel M, et al. Natural polyreactive IgA antibodies coat the intestinal microbiota. Science. 2017;
29. Christmann B S, Abrahamsson T R, Bernstein C N, Duck L W, Mannon P J, Berg G, et al. Human seroreactivity to gut microbiota antigens. J Allergy Clin Immunol. 2015; 136:1378-1386-5.
30. Bunker J J, Flynn T M, Koval J C, Shaw D G, Meisel M, McDonald B D, et al. Innate and Adaptive Humoral Responses Coat Distinct Commensal Bacteria with Immunoglobulin A. Immunity. 2015; 43:541-53.

31. Okai S, Usui F, Yokota S, Hori-i Y, Hasegawa M, Nakamura T, et al. High-affinity monoclonal IgA regulates gut microbiota and prevents colitis in mice. Nat Microbiol. 2016; 1:16103.

32. Rollenske T, Szijarto V, Lukasiewicz J, Guachalla L M, Stojkovic K, Hartl K, et al. Cross-specificity of protective human antibodies against *Klebsiella pneumoniae* LPS 0-antigen. Nat Immunol. 2018; 19:617-24.

33. Jorgensen S F, Troseid M, Kummen M, Anmarkrud J A, Michelsen A E, Osnes L T, et al. Altered gut microbiota profile in common variable immunodeficiency associates with levels of lipopolysaccharide and markers of systemic immune activation. Mucosal Immunol. 2016; 9:1455-65.

34. Favre O, Leimgruber A, Nicole A, Spertini F. Intravenous immunoglobulin replacement prevents severe and lower respiratory tract infections, but not upper respiratory tract and non-respiratory infections in common variable immune deficiency. Allergy. 2005; 60:385-90.

35. Gomez de Agüero M, Ganal-Vonarburg S C, Fuhrer T, Rupp S, Uchimura Y, Li H, et al. The maternal microbiota drives early postnatal innate immune development. Science. 2016; 351:1296-302.

36. Sandolo C, Péchiné S, Le Monnier A, Hoys S, Janoir C, Coviello T, et al. Encapsulation of Cwp84 into pectin beads for oral vaccination against *Clostridium difficile*. Eur J Pharm Biopharm Off J Arbeitsgemeinschaft Pharm Verfahrenstechnik E V. 2011; 79:566-73.

37. Juste C, Kreil D P, Beauvallet C, Guillot A, Vaca S, Carapito C, et al. Bacterial protein signals are associated with Crohn's disease. Gut. 2014; 63:1566-77.

38. Caporaso J G, Kuczynski J, Stombaugh J, Bittinger K, Bushman F D, Costello E K, et al. QIIME allows analysis of high-throughput community sequencing data. Nat Methods. 2010; 7:335-6.

39. Cole J R, Wang Q, Cardenas E, Fish J, Chai B, Farris R J, et al. The Ribosomal Database Project: improved alignments and new tools for rRNA analysis. Nucleic Acids Res. 2009; 37:D141-145.

The invention claimed is:

1. A method of treating an antibody deficiency in a subject in need thereof, comprising
   administering to the subject a composition comprising IgA (immunoglobulins A)
   wherein the composition is administered orally,
   wherein the composition contains at least two different monoclonal IgA that are cross-reactive and bind to multiple bacterial targets,
   and wherein the antibody deficiency is
   a primary antibody deficiency that is SIgAd (Selective IgA deficiency) or common variable immunodeficiency (CVID); or
   a secondary antibody deficiency that is myeloma, Chronic Lymphocitic Leukemia (CLL), or an immune deficiency induced by a medical treatment.

2. The method according to claim 1, wherein said primary antibody deficiency is SIgAd (Selective IgA deficiency).

3. The method according to claim 1, wherein said primary antibody deficiency is common variable immunodeficiency (CVID).

4. The method according to claim 1, wherein the immune deficiency induced by a medical treatment is an antibody deficiency induced by immunosuppressive drugs or cytostatic drugs.

* * * * *

UNITED STATES PATENT AND TRADEMARK OFFICE
CERTIFICATE OF CORRECTION

| | | |
|---|---|---|
| PATENT NO. | : 11,718,661 B2 | Page 1 of 1 |
| APPLICATION NO. | : 17/288013 | |
| DATED | : August 8, 2023 | |
| INVENTOR(S) | : Guy Gorochov | |

It is certified that error appears in the above-identified patent and that said Letters Patent is hereby corrected as shown below:

On the Title Page

Left Column (Item (73) Assignees), Line 19 (approx.), change "INSERM (Instut" to --INSERM (Institut--.

Signed and Sealed this
Seventh Day of November, 2023

Katherine Kelly Vidal
*Director of the United States Patent and Trademark Office*